US011773145B2

(12) United States Patent
Liu et al.

(10) Patent No.: US 11,773,145 B2
(45) Date of Patent: Oct. 3, 2023

(54) TOPICAL COMPOSITIONS AND USES

(71) Applicant: ShanghaiTech University, Pudong New Area (CN)

(72) Inventors: Jia Liu, Shanghai (CN); Biao Jiang, Shanghai (CN)

(73) Assignee: ShanghaiTech University, Shanghai (CN)

( * ) Notice: Subject to any disclaimer, the term of this patent is extended or adjusted under 35 U.S.C. 154(b) by 0 days.

(21) Appl. No.: 16/632,299

(22) PCT Filed: Jul. 20, 2018

(86) PCT No.: PCT/CN2018/096448
§ 371 (c)(1),
(2) Date: Jan. 17, 2020

(87) PCT Pub. No.: WO2019/015673
PCT Pub. Date: Jan. 24, 2019

(65) Prior Publication Data
US 2020/0231634 A1 Jul. 23, 2020

(30) Foreign Application Priority Data
Jul. 21, 2017 (WO) ................ PCT/CN2017/093810

(51) Int. Cl.
C07K 14/33 (2006.01)
C07K 19/00 (2006.01)
A61K 38/00 (2006.01)

(52) U.S. Cl.
CPC .............. *C07K 14/33* (2013.01); *C07K 19/00* (2013.01); *A61K 38/00* (2013.01); *C07K 2319/55* (2013.01); *C07K 2319/81* (2013.01)

(58) Field of Classification Search
CPC ........ A61K 39/00; A61K 39/02; A61K 39/08; A61K 2039/55544; A61K 38/00; C07K 14/33; C07K 19/00; C07K 2319/55; C07K 2319/81
USPC ..... 424/9.1, 9.2, 184.1, 185.1, 234.1, 236.1, 424/247.1
See application file for complete search history.

(56) References Cited

U.S. PATENT DOCUMENTS

| 2008/0107690 A1 | 5/2008 | Dake et al. |
| 2011/0059187 A1 | 3/2011 | Basu et al. |

FOREIGN PATENT DOCUMENTS

| CN | 1470520 A | 1/2004 |
| CN | 106459155 A | 2/2017 |
| JP | 2006-320221 A | 11/2006 |
| JP | 2006320221 A | 11/2006 |
| JP | 2007526340 A | 9/2007 |
| JP | 2012528596 A | 11/2012 |
| WO | WO 2005/084410 | 9/2005 |
| WO | WO 2005/084410 A2 | 9/2005 |
| WO | WO2005117928 A1 | 12/2005 |
| WO | WO 2010/141724 A2 | 12/2010 |
| WO | WO2015188094 A1 | 12/2015 |

OTHER PUBLICATIONS

Amani, et al. Designing and analyzing the structure of Tat-BoNT/A(1-448) fusion protein: An in silico approach. Mol Biol Res Commun. Jun. 2014;3(2):115-127.
Gaj, et al. Direct Protein Delivery to Mammalian Cells Using Cell-permeable Cys2-His2 Zinc-finger Domains. J Vis Exp. Mar. 25, 2015;(97) Article e52814. p. 1-7.
Gaj, et al. Protein delivery using Cys2-His2 zinc-finger domains. ACS Chem Biol. Aug. 15, 2014;9(8):1662-7.
International Search Report & Written Opinion dated Sep. 28, 2018 for PCT/CN2018/096448. 13 pages.
Kim, et al. Expression, purification and transduction of PEP-1-botulinum neurotoxin type A (PEP-1-BoNT/A) into skin. J Biochem Mol Biol. Sep. 30, 2006;39(5):642-7.
Pickett, et al. Towards new uses of botulinum toxin as a novel therapeutic tool. Toxins (Basel). Jan. 2011;3(1):63-81.
Extended European Search Report, European Patent Application 18 834 986.4, dated Mar. 29, 2021, 10 pages.
Dae Won Kim et al. "Expression, purification and transduction of PEP-1-botulinum neurotoxin type A (PEP-1-BoNT/A) into skin", Journal of Biochemistry and Molecular Biology, vol. 39, No. 5, Sep. 2006 (Sep. 2006). XP055076669 (6 pages).
Thomas Gaj et al. "Direct Protein Delivery to Mammalian Cells Using Cell-permeable Cys$_2$-His$_2$ Zinc-finger Domains", Journal of Visualized Experiments, vol. 973791, No. 97, Jan. 2015 (Jan. 2015), XP055565466 (8 pages).
Jensen M J et al. "Expression, Purification, and Efficacy of the Type A Botulinum Neurotoxin Catalytic Domain Fused to Two Translocation Domain Variants", Toxicon, Elmsford, NY, US, vol. 41, No. 6, May 2003 (May 2003), pp. 691-701, XP001156776, ISSN: 0041-0101 (12 pages).
Baldwin M R et al. "The C-terminus of botulinum neurotoxin type A light chain contributes to solubility, catalysis, and stability", Protein Expression and Purification, Academic Press, San and Diego, CA, vol. 37, No. 1, Sep. 2004, (Sep. 2004), pp. 187-195, XP004523954 (10 pages).

*Primary Examiner* — Robert A Zeman
(74) *Attorney, Agent, or Firm* — Sheppard Mullin Richter & Hampton LLP

(57) ABSTRACT

Provided are chimeric polypeptides that include one or more zinc finger motifs fused to a therapeutic peptide such as botulinum neurotoxins (BoNTs). The zinc finger motif may be located at the C-terminal side of the BoNT and the chimeric polypeptide can optionally include two or more such zinc finger motifs. It said the disclosed chimeric polypeptides can be efficiently delivered to a subject transdermally.

18 Claims, 6 Drawing Sheets
Specification includes a Sequence Listing.

His-FL (SEQ ID NO:10)
Protein ID: 1

| His₆ | BoNTA-LC | BoNTA-HC |

His-ZFP₃-LC (SEQ ID NO:11)
Protein ID: 2

| His₆ | ZFP₃ | BoNTA-LC |

His-ZFP₃-FL (SEQ ID NO:12)
Protein ID: 3

| His₆ | ZFP₃ | BoNTA-LC | BoNTA-HC |

LC-ZFP₃-His (SEQ ID NO:13)
Protein ID: 4

| BoNTA-LC | ZFP₃ | His₆ |

FL-ZFP₃-His (SEQ ID NO:14)
Protein ID: 5

| BoNTA-LC | BoNTA-HC | ZFP₃ | His₆ |

His-ZFP₃-FL-ZFP₃ (SEQ ID NO:15)
Protein ID: 6

| His₆ | ZFP₃ | BoNTA-LC | BoNTA-HC | ZFP₃ |

TAT-FL-His (SEQ ID NO:16)
Protein ID: 7

| His₆ | TAT | BoNTA-LC | BoNTA-HC |

Pep1-FL-His (SEQ ID NO:17)
Protein ID: 8

| His₆ | Pep-1 | BoNTA-LC | BoNTA-HC |

SEQUENCE LISTING

<160> NUMBER OF SEQ ID NOS: 19

<210> SEQ ID NO 1
<211> LENGTH: 28
<212> TYPE: PRT
<213> ORGANISM: Artificial Sequence
<220> FEATURE:
<223> OTHER INFORMATION: Synthetic

<400> SEQUENCE: 1

Glu Lys Pro Tyr Lys Cys Pro Glu Cys Gly Lys Ser Phe Ser Ala Ser
1               5                   10                  15

Ala Ala Leu Val Ala His Gln Arg Thr His Thr Gly
            20                  25

<210> SEQ ID NO 2
<211> LENGTH: 56
<212> TYPE: PRT
<213> ORGANISM: Artificial Sequence
<220> FEATURE:
<223> OTHER INFORMATION: Synthetic

<400> SEQUENCE: 2

Glu Lys Pro Tyr Lys Cys Pro Glu Cys Gly Lys Ser Phe Ser Ala Ser
1               5                   10                  15

Ala Ala Leu Val Ala His Gln Arg Thr His Thr Gly Glu Lys Pro Tyr
            20                  25                  30

Lys Cys Pro Glu Cys Gly Lys Ser Phe Ser Ala Ser Ala Ala Leu Val
        35                  40                  45

Ala His Gln Arg Thr His Thr Gly
    50                  55

<210> SEQ ID NO 3
<211> LENGTH: 84
<212> TYPE: PRT
<213> ORGANISM: Artificial Sequence
<220> FEATURE:
<223> OTHER INFORMATION: Synthetic

<400> SEQUENCE: 3

Glu Lys Pro Tyr Lys Cys Pro Glu Cys Gly Lys Ser Phe Ser Ala Ser
1               5                   10                  15

Ala Ala Leu Val Ala His Gln Arg Thr His Thr Gly Glu Lys Pro Tyr
            20                  25                  30

Lys Cys Pro Glu Cys Gly Lys Ser Phe Ser Ala Ser Ala Ala Leu Val
        35                  40                  45

Ala His Gln Arg Thr His Thr Gly Glu Lys Pro Tyr Lys Cys Pro Glu
    50                  55                  60

Cys Gly Lys Ser Phe Ser Ala Ser Ala Ala Leu Val Ala His Gln Arg
65                  70                  75                  80

Thr His Thr Gly

<210> SEQ ID NO 4
<211> LENGTH: 112
<212> TYPE: PRT
<213> ORGANISM: Artificial Sequence
<220> FEATURE:
<223> OTHER INFORMATION: Synthetic

<400> SEQUENCE: 4

Glu Lys Pro Tyr Lys Cys Pro Glu Cys Gly Lys Ser Phe Ser Ala Ser
1               5                   10                  15

```
Ala Ala Leu Val Ala His Gln Arg Thr His Thr Gly Glu Lys Pro Tyr
            20                  25                  30

Lys Cys Pro Glu Cys Gly Lys Ser Phe Ser Ala Ser Ala Ala Leu Val
        35                  40                  45

Ala His Gln Arg Thr His Thr Gly Glu Lys Pro Tyr Lys Cys Pro Glu
    50                  55                  60

Cys Gly Lys Ser Phe Ser Ala Ser Ala Ala Leu Val Ala His Gln Arg
65                  70                  75                  80

Thr His Thr Gly Glu Lys Pro Tyr Lys Cys Pro Glu Cys Gly Lys Ser
                85                  90                  95

Phe Ser Ala Ser Ala Ala Leu Val Ala His Gln Arg Thr His Thr Gly
            100                 105                 110
```

<210> SEQ ID NO 5
<211> LENGTH: 38
<212> TYPE: PRT
<213> ORGANISM: Artificial Sequence
<220> FEATURE:
<223> OTHER INFORMATION: Synthetic

<400> SEQUENCE: 5

```
Arg Ile Pro Leu Ser Cys Thr Ile Cys Arg Lys Arg Lys Val Lys Cys
1               5                   10                  15

Asp Lys Leu Arg Pro His Cys Gln Gln Cys Thr Lys Thr Gly Val Ala
            20                  25                  30

His Leu Cys His Tyr Met
        35
```

<210> SEQ ID NO 6
<211> LENGTH: 17
<212> TYPE: PRT
<213> ORGANISM: Artificial Sequence
<220> FEATURE:
<223> OTHER INFORMATION: Synthetic

<400> SEQUENCE: 6

```
Thr Cys Tyr Asn Cys Gly Gln Thr Gly His Leu Ser Arg Glu Cys Pro
1               5                   10                  15

Ser
```

<210> SEQ ID NO 7
<211> LENGTH: 52
<212> TYPE: PRT
<213> ORGANISM: Artificial Sequence
<220> FEATURE:
<223> OTHER INFORMATION: Synthetic

<400> SEQUENCE: 7

```
Arg Arg Cys Asn Cys Met Ala Thr Arg His Pro Leu Phe Glu Val Ala
1               5                   10                  15

Pro Asn Cys Leu Asn Cys Gly Lys Ile Ile Cys Glu Lys Glu Gly Leu
            20                  25                  30

Gln Pro Cys Ser Tyr Cys Gly Gln Glu Leu Leu Ser Pro Lys Asp Lys
        35                  40                  45

Gln Glu Ile Ile
    50
```

<210> SEQ ID NO 8
<211> LENGTH: 425
<212> TYPE: PRT

<213> ORGANISM: Artificial Sequence
<220> FEATURE:
<223> OTHER INFORMATION: Synthetic

<400> SEQUENCE: 8

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
```

```
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe
                420                 425

<210> SEQ ID NO 9
<211> LENGTH: 871
<212> TYPE: PRT
<213> ORGANISM: Artificial Sequence
<220> FEATURE:
<223> OTHER INFORMATION: Synthetic

<400> SEQUENCE: 9

Tyr Lys Leu Leu Cys Val Arg Gly Ile Ile Thr Ser Lys Thr Lys Ser
1               5                   10                  15

Leu Asp Lys Gly Tyr Asn Lys Ala Leu Asn Asp Leu Cys Ile Lys Val
                20                  25                  30

Asn Asn Trp Asp Leu Phe Phe Ser Pro Ser Glu Asp Asn Phe Thr Asn
            35                  40                  45

Asp Leu Asn Lys Gly Glu Glu Ile Thr Ser Asp Thr Asn Ile Glu Ala
        50                  55                  60

Ala Glu Glu Asn Ile Ser Leu Asp Leu Ile Gln Gln Tyr Tyr Leu Thr
65                  70                  75                  80

Phe Asn Phe Asp Asn Glu Pro Glu Asn Ile Ser Ile Glu Asn Leu Ser
                85                  90                  95

Ser Asp Ile Ile Gly Gln Leu Glu Leu Met Pro Asn Ile Glu Arg Phe
            100                 105                 110

Pro Asn Gly Lys Lys Tyr Glu Leu Asp Lys Tyr Thr Met Phe His Tyr
        115                 120                 125

Leu Arg Ala Gln Glu Phe Glu His Gly Lys Ser Arg Ile Ala Leu Thr
    130                 135                 140

Asn Ser Val Asn Glu Ala Leu Leu Asn Pro Ser Arg Val Tyr Thr Phe
145                 150                 155                 160

Phe Ser Ser Asp Tyr Val Lys Lys Val Asn Lys Ala Thr Glu Ala Ala
                165                 170                 175

Met Phe Leu Gly Trp Val Glu Gln Leu Val Tyr Asp Phe Thr Asp Glu
            180                 185                 190

Thr Ser Glu Val Ser Thr Thr Asp Lys Ile Ala Asp Ile Thr Ile Ile
        195                 200                 205

Ile Pro Tyr Ile Gly Pro Ala Leu Asn Ile Gly Asn Met Leu Tyr Lys
    210                 215                 220

Asp Asp Phe Val Gly Ala Leu Ile Phe Ser Gly Ala Val Ile Leu Leu
225                 230                 235                 240

Glu Phe Ile Pro Glu Ile Ala Ile Pro Val Leu Gly Thr Phe Ala Leu
                245                 250                 255

Val Ser Tyr Ile Ala Asn Lys Val Leu Thr Val Gln Thr Ile Asp Asn
            260                 265                 270

Ala Leu Ser Lys Arg Asn Glu Lys Trp Asp Glu Val Tyr Lys Tyr Ile
        275                 280                 285

Val Thr Asn Trp Leu Ala Lys Val Asn Thr Gln Ile Asp Leu Ile Arg
    290                 295                 300

Lys Lys Met Lys Glu Ala Leu Glu Asn Gln Ala Glu Ala Thr Lys Ala
305                 310                 315                 320

Ile Ile Asn Tyr Gln Tyr Asn Gln Tyr Thr Glu Glu Glu Lys Asn Asn
```

```
                    325                 330                 335
Ile Asn Phe Asn Ile Asp Asp Leu Ser Ser Lys Leu Asn Glu Ser Ile
                340                 345                 350
Asn Lys Ala Met Ile Asn Ile Asn Lys Phe Leu Asn Gln Cys Ser Val
                355                 360                 365
Ser Tyr Leu Met Asn Ser Met Ile Pro Tyr Gly Val Lys Arg Leu Glu
            370                 375                 380
Asp Phe Asp Ala Ser Leu Lys Asp Ala Leu Leu Lys Tyr Ile Tyr Asp
385                 390                 395                 400
Asn Arg Gly Thr Leu Ile Gly Gln Val Asp Arg Leu Lys Asp Lys Val
                405                 410                 415
Asn Asn Thr Leu Ser Thr Asp Ile Pro Phe Gln Leu Ser Lys Tyr Val
                420                 425                 430
Asp Asn Gln Arg Leu Leu Ser Thr Phe Thr Glu Tyr Ile Lys Asn Ile
                435                 440                 445
Ile Asn Thr Ser Ile Leu Asn Leu Arg Tyr Glu Ser Asn His Leu Ile
                450                 455                 460
Asp Leu Ser Arg Tyr Ala Ser Lys Ile Asn Ile Gly Ser Lys Val Asn
465                 470                 475                 480
Phe Asp Pro Ile Asp Lys Asn Gln Ile Gln Leu Phe Asn Leu Glu Ser
                    485                 490                 495
Ser Lys Ile Glu Val Ile Leu Lys Asn Ala Ile Val Tyr Asn Ser Met
                500                 505                 510
Tyr Glu Asn Phe Ser Thr Ser Phe Trp Ile Arg Ile Pro Lys Tyr Phe
            515                 520                 525
Asn Ser Ile Ser Leu Asn Asn Glu Tyr Thr Ile Ile Asn Cys Met Glu
        530                 535                 540
Asn Asn Ser Gly Trp Lys Val Ser Leu Asn Tyr Gly Glu Ile Ile Trp
545                 550                 555                 560
Thr Leu Gln Asp Thr Gln Glu Ile Lys Gln Arg Val Val Phe Lys Tyr
                565                 570                 575
Ser Gln Met Ile Asn Ile Ser Asp Tyr Ile Asn Arg Trp Ile Phe Val
            580                 585                 590
Thr Ile Thr Asn Asn Arg Leu Asn Asn Ser Lys Ile Tyr Ile Asn Gly
        595                 600                 605
Arg Leu Ile Asp Gln Lys Pro Ile Ser Asn Leu Gly Asn Ile His Ala
    610                 615                 620
Ser Asn Asn Ile Met Phe Lys Leu Asp Gly Cys Arg Asp Thr His Arg
625                 630                 635                 640
Tyr Ile Trp Ile Lys Tyr Phe Asn Leu Phe Asp Lys Glu Leu Asn Glu
                645                 650                 655
Lys Glu Ile Lys Asp Leu Tyr Asp Asn Gln Ser Asn Ser Gly Ile Leu
            660                 665                 670
Lys Asp Phe Trp Gly Asp Tyr Leu Gln Tyr Asp Lys Pro Tyr Tyr Met
        675                 680                 685
Leu Asn Leu Tyr Asp Pro Asn Lys Tyr Val Asp Val Asn Asn Val Gly
    690                 695                 700
Ile Arg Gly Tyr Met Tyr Leu Lys Gly Pro Arg Gly Ser Val Met Thr
705                 710                 715                 720
Thr Asn Ile Tyr Leu Asn Ser Ser Leu Tyr Arg Gly Thr Lys Phe Ile
                725                 730                 735
Ile Lys Lys Tyr Ala Ser Gly Asn Lys Asp Asn Ile Val Arg Asn Asn
            740                 745                 750
```

```
Asp Arg Val Tyr Ile Asn Val Val Lys Asn Lys Glu Tyr Arg Leu
            755                 760                 765

Ala Thr Asn Ala Ser Gln Ala Gly Val Glu Lys Ile Leu Ser Ala Leu
770                 775                 780

Glu Ile Pro Asp Val Gly Asn Leu Ser Gln Val Val Met Lys Ser
785                 790                 795                 800

Lys Asn Asp Gln Gly Ile Thr Asn Lys Cys Lys Met Asn Leu Gln Asp
                805                 810                 815

Asn Asn Gly Asn Asp Ile Gly Phe Ile Gly Phe His Gln Phe Asn Asn
                820                 825                 830

Ile Ala Lys Leu Val Ala Ser Asn Trp Tyr Asn Arg Gln Ile Glu Arg
                835                 840                 845

Ser Ser Arg Thr Leu Gly Cys Ser Trp Glu Phe Ile Pro Val Asp Asp
            850                 855                 860

Gly Trp Gly Glu Arg Pro Leu
865                 870

<210> SEQ ID NO 10
<211> LENGTH: 1312
<212> TYPE: PRT
<213> ORGANISM: Artificial Sequence
<220> FEATURE:
<223> OTHER INFORMATION: Synthetic

<400> SEQUENCE: 10

Met His His His His His Gly Gly Ser Gly Gly Ser Gly Gly Ser
1               5                   10                  15

Met Pro Phe Val Asn Lys Gln Phe Asn Tyr Lys Asp Pro Val Asn Gly
                20                  25                  30

Val Asp Ile Ala Tyr Ile Lys Ile Pro Asn Val Gly Gln Met Gln Pro
            35                  40                  45

Val Lys Ala Phe Lys Ile His Asn Lys Ile Trp Val Ile Pro Glu Arg
50                  55                  60

Asp Thr Phe Thr Asn Pro Glu Glu Gly Asp Leu Asn Pro Pro Pro Glu
65                  70                  75                  80

Ala Lys Gln Val Pro Val Ser Tyr Tyr Asp Ser Thr Tyr Leu Ser Thr
                85                  90                  95

Asp Asn Glu Lys Asp Asn Tyr Leu Lys Gly Val Thr Lys Leu Phe Glu
                100                 105                 110

Arg Ile Tyr Ser Thr Asp Leu Gly Arg Met Leu Leu Thr Ser Ile Val
            115                 120                 125

Arg Gly Ile Pro Phe Trp Gly Gly Ser Thr Ile Asp Thr Glu Leu Lys
130                 135                 140

Val Ile Asp Thr Asn Cys Ile Asn Val Ile Gln Pro Asp Gly Ser Tyr
145                 150                 155                 160

Arg Ser Glu Glu Leu Asn Leu Val Ile Ile Gly Pro Ser Ala Asp Ile
                165                 170                 175

Ile Gln Phe Glu Cys Lys Ser Phe Gly His Glu Val Leu Asn Leu Thr
                180                 185                 190

Arg Asn Gly Tyr Gly Ser Thr Gln Tyr Ile Arg Phe Ser Pro Asp Phe
            195                 200                 205

Thr Phe Gly Phe Glu Glu Ser Leu Glu Val Asp Thr Asn Pro Leu Leu
210                 215                 220

Gly Ala Gly Lys Phe Ala Thr Asp Pro Ala Val Thr Leu Ala His Glu
225                 230                 235                 240
```

```
Leu Ile His Ala Gly His Arg Leu Tyr Gly Ile Ala Ile Asn Pro Asn
                245                 250                 255

Arg Val Phe Lys Val Asn Thr Asn Ala Tyr Tyr Glu Met Ser Gly Leu
            260                 265                 270

Glu Val Ser Phe Glu Glu Leu Arg Thr Phe Gly Gly His Asp Ala Lys
        275                 280                 285

Phe Ile Asp Ser Leu Gln Glu Asn Glu Phe Arg Leu Tyr Tyr Tyr Asn
    290                 295                 300

Lys Phe Lys Asp Ile Ala Ser Thr Leu Asn Lys Ala Lys Ser Ile Val
305                 310                 315                 320

Gly Thr Thr Ala Ser Leu Gln Tyr Met Lys Asn Val Phe Lys Glu Lys
                325                 330                 335

Tyr Leu Leu Ser Glu Asp Thr Ser Gly Lys Phe Ser Val Asp Lys Leu
            340                 345                 350

Lys Phe Asp Lys Leu Tyr Lys Met Leu Thr Glu Ile Tyr Thr Glu Asp
        355                 360                 365

Asn Phe Val Lys Phe Phe Lys Val Leu Asn Arg Lys Thr Tyr Leu Asn
    370                 375                 380

Phe Asp Lys Ala Val Phe Lys Ile Asn Ile Val Pro Lys Val Asn Tyr
385                 390                 395                 400

Thr Ile Tyr Asp Gly Phe Asn Leu Arg Asn Thr Asn Leu Ala Ala Asn
                405                 410                 415

Phe Asn Gly Gln Asn Thr Glu Ile Asn Asn Met Asn Phe Thr Lys Leu
            420                 425                 430

Lys Asn Phe Thr Gly Leu Phe Glu Phe Tyr Lys Leu Leu Cys Val Arg
        435                 440                 445

Gly Ile Ile Thr Ser Lys Thr Lys Ser Leu Asp Lys Gly Tyr Asn Lys
    450                 455                 460

Ala Leu Asn Asp Leu Cys Ile Lys Val Asn Asn Trp Asp Leu Phe Phe
465                 470                 475                 480

Ser Pro Ser Glu Asp Asn Phe Thr Asn Asp Leu Asn Lys Gly Glu Glu
                485                 490                 495

Ile Thr Ser Asp Thr Asn Ile Glu Ala Ala Glu Glu Asn Ile Ser Leu
            500                 505                 510

Asp Leu Ile Gln Gln Tyr Tyr Leu Thr Phe Asn Phe Asp Asn Glu Pro
        515                 520                 525

Glu Asn Ile Ser Ile Glu Asn Leu Ser Ser Asp Ile Ile Gly Gln Leu
    530                 535                 540

Glu Leu Met Pro Asn Ile Glu Arg Phe Pro Asn Gly Lys Lys Tyr Glu
545                 550                 555                 560

Leu Asp Lys Tyr Thr Met Phe His Tyr Leu Arg Ala Gln Glu Phe Glu
                565                 570                 575

His Gly Lys Ser Arg Ile Ala Leu Thr Asn Ser Val Asn Glu Ala Leu
            580                 585                 590

Leu Asn Pro Ser Arg Val Tyr Thr Phe Phe Ser Ser Asp Tyr Val Lys
        595                 600                 605

Lys Val Asn Lys Ala Thr Glu Ala Ala Met Phe Leu Gly Trp Val Glu
    610                 615                 620

Gln Leu Val Tyr Asp Phe Thr Asp Glu Thr Ser Glu Val Ser Thr Thr
625                 630                 635                 640

Asp Lys Ile Ala Asp Ile Thr Ile Ile Pro Tyr Ile Gly Pro Ala
                645                 650                 655
```

-continued

```
Leu Asn Ile Gly Asn Met Leu Tyr Lys Asp Asp Phe Val Gly Ala Leu
            660                 665                 670
Ile Phe Ser Gly Ala Val Ile Leu Leu Glu Phe Ile Pro Glu Ile Ala
        675                 680                 685
Ile Pro Val Leu Gly Thr Phe Ala Leu Val Ser Tyr Ile Ala Asn Lys
    690                 695                 700
Val Leu Thr Val Gln Thr Ile Asp Asn Ala Leu Ser Lys Arg Asn Glu
705                 710                 715                 720
Lys Trp Asp Glu Val Tyr Lys Tyr Ile Val Thr Asn Trp Leu Ala Lys
                725                 730                 735
Val Asn Thr Gln Ile Asp Leu Ile Arg Lys Lys Met Lys Glu Ala Leu
            740                 745                 750
Glu Asn Gln Ala Glu Ala Thr Lys Ala Ile Ile Asn Tyr Gln Tyr Asn
        755                 760                 765
Gln Tyr Thr Glu Glu Lys Asn Asn Ile Asn Phe Asn Ile Asp Asp
    770                 775                 780
Leu Ser Ser Lys Leu Asn Glu Ser Ile Asn Lys Ala Met Ile Asn Ile
785                 790                 795                 800
Asn Lys Phe Leu Asn Gln Cys Ser Val Ser Tyr Leu Met Asn Ser Met
                805                 810                 815
Ile Pro Tyr Gly Val Lys Arg Leu Glu Asp Phe Asp Ala Ser Leu Lys
            820                 825                 830
Asp Ala Leu Leu Lys Tyr Ile Tyr Asp Asn Arg Gly Thr Leu Ile Gly
        835                 840                 845
Gln Val Asp Arg Leu Lys Asp Lys Val Asn Asn Thr Leu Ser Thr Asp
    850                 855                 860
Ile Pro Phe Gln Leu Ser Lys Tyr Val Asp Asn Gln Arg Leu Leu Ser
865                 870                 875                 880
Thr Phe Thr Glu Tyr Ile Lys Asn Ile Ile Asn Thr Ser Ile Leu Asn
                885                 890                 895
Leu Arg Tyr Glu Ser Asn His Leu Ile Asp Leu Ser Arg Tyr Ala Ser
            900                 905                 910
Lys Ile Asn Ile Gly Ser Lys Val Asn Phe Asp Pro Ile Asp Lys Asn
        915                 920                 925
Gln Ile Gln Leu Phe Asn Leu Glu Ser Ser Lys Ile Glu Val Ile Leu
    930                 935                 940
Lys Asn Ala Ile Val Tyr Asn Ser Met Tyr Glu Asn Phe Ser Thr Ser
945                 950                 955                 960
Phe Trp Ile Arg Ile Pro Lys Tyr Phe Asn Ser Ile Ser Leu Asn Asn
                965                 970                 975
Glu Tyr Thr Ile Ile Asn Cys Met Glu Asn Asn Ser Gly Trp Lys Val
            980                 985                 990
Ser Leu Asn Tyr Gly Glu Ile Ile Trp Thr Leu Gln Asp Thr Gln Glu
        995                 1000                1005
Ile Lys Gln Arg Val Val Phe Lys Tyr Ser Gln Met Ile Asn Ile
    1010                1015                1020
Ser Asp Tyr Ile Asn Arg Trp Ile Phe Val Thr Ile Thr Asn Asn
    1025                1030                1035
Arg Leu Asn Asn Ser Lys Ile Tyr Ile Asn Gly Arg Leu Ile Asp
    1040                1045                1050
Gln Lys Pro Ile Ser Asn Leu Gly Asn Ile His Ala Ser Asn Asn
    1055                1060                1065
Ile Met Phe Lys Leu Asp Gly Cys Arg Asp Thr His Arg Tyr Ile
```

-continued

```
              1070                1075                1080

Trp Ile Lys Tyr Phe Asn Leu Phe Asp Lys Glu Leu Asn Glu Lys
        1085                1090                1095

Glu Ile Lys Asp Leu Tyr Asp Asn Gln Ser Asn Ser Gly Ile Leu
        1100                1105            1110

Lys Asp Phe Trp Gly Asp Tyr Leu Gln Tyr Asp Lys Pro Tyr Tyr
        1115                1120                1125

Met Leu Asn Leu Tyr Asp Pro Asn Lys Tyr Val Asp Val Asn Asn
        1130                1135            1140

Val Gly Ile Arg Gly Tyr Met Tyr Leu Lys Gly Pro Arg Gly Ser
        1145                1150                1155

Val Met Thr Thr Asn Ile Tyr Leu Asn Ser Ser Leu Tyr Arg Gly
        1160                1165            1170

Thr Lys Phe Ile Ile Lys Lys Tyr Ala Ser Gly Asn Lys Asp Asn
        1175                1180            1185

Ile Val Arg Asn Asn Asp Arg Val Tyr Ile Asn Val Val Val Lys
        1190                1195                1200

Asn Lys Glu Tyr Arg Leu Ala Thr Asn Ala Ser Gln Ala Gly Val
        1205                1210            1215

Glu Lys Ile Leu Ser Ala Leu Glu Ile Pro Asp Val Gly Asn Leu
        1220                1225                1230

Ser Gln Val Val Val Met Lys Ser Lys Asn Asp Gln Gly Ile Thr
        1235                1240            1245

Asn Lys Cys Lys Met Asn Leu Gln Asp Asn Asn Gly Asn Asp Ile
        1250                1255            1260

Gly Phe Ile Gly Phe His Gln Phe Asn Asn Ile Ala Lys Leu Val
        1265                1270            1275

Ala Ser Asn Trp Tyr Asn Arg Gln Ile Glu Arg Ser Ser Arg Thr
        1280                1285            1290

Leu Gly Cys Ser Trp Glu Phe Ile Pro Val Asp Asp Gly Trp Gly
        1295                1300                1305

Glu Arg Pro Leu
        1310

<210> SEQ ID NO 11
<211> LENGTH: 534
<212> TYPE: PRT
<213> ORGANISM: Artificial Sequence
<220> FEATURE:
<223> OTHER INFORMATION: Synthetic

<400> SEQUENCE: 11

Met His His His His His Gly Gly Ser Gly Gly Ser Gly Gly Ser
1               5                   10                  15

Glu Lys Pro Tyr Lys Cys Pro Glu Cys Gly Lys Ser Phe Ser Ala Ser
            20                  25                  30

Ala Ala Leu Val Ala His Gln Arg Thr His Thr Gly Glu Lys Pro Tyr
        35                  40                  45

Lys Cys Pro Glu Cys Gly Lys Ser Phe Ser Ala Ser Ala Ala Leu Val
    50                  55                  60

Ala His Gln Arg Thr His Thr Gly Glu Lys Pro Tyr Lys Cys Pro Glu
65                  70                  75                  80

Cys Gly Lys Ser Phe Ser Ala Ser Ala Ala Leu Val Ala His Gln Arg
                85                  90                  95

Thr His Thr Gly Gly Gly Ser Gly Gly Ser Gly Gly Ser Met Pro Phe
```

```
                    100                 105                 110
Val Asn Lys Gln Phe Asn Tyr Lys Asp Pro Val Asn Gly Val Asp Ile
            115                 120                 125
Ala Tyr Ile Lys Ile Pro Asn Val Gly Gln Met Gln Pro Val Lys Ala
            130                 135                 140
Phe Lys Ile His Asn Lys Ile Trp Val Ile Pro Glu Arg Asp Thr Phe
145                 150                 155                 160
Thr Asn Pro Glu Glu Gly Asp Leu Asn Pro Pro Glu Ala Lys Gln
                    165                 170                 175
Val Pro Val Ser Tyr Tyr Asp Ser Thr Tyr Leu Ser Thr Asp Asn Glu
            180                 185                 190
Lys Asp Asn Tyr Leu Lys Gly Val Thr Lys Leu Phe Glu Arg Ile Tyr
            195                 200                 205
Ser Thr Asp Leu Gly Arg Met Leu Leu Thr Ser Ile Val Arg Gly Ile
            210                 215                 220
Pro Phe Trp Gly Gly Ser Thr Ile Asp Thr Glu Leu Lys Val Ile Asp
225                 230                 235                 240
Thr Asn Cys Ile Asn Val Ile Gln Pro Asp Gly Ser Tyr Arg Ser Glu
                    245                 250                 255
Glu Leu Asn Leu Val Ile Ile Gly Pro Ser Ala Asp Ile Ile Gln Phe
            260                 265                 270
Glu Cys Lys Ser Phe Gly His Glu Val Leu Asn Leu Thr Arg Asn Gly
            275                 280                 285
Tyr Gly Ser Thr Gln Tyr Ile Arg Phe Ser Pro Asp Phe Thr Phe Gly
            290                 295                 300
Phe Glu Glu Ser Leu Glu Val Asp Thr Asn Pro Leu Leu Gly Ala Gly
305                 310                 315                 320
Lys Phe Ala Thr Asp Pro Ala Val Thr Leu Ala His Glu Leu Ile His
                    325                 330                 335
Ala Gly His Arg Leu Tyr Gly Ile Ala Ile Asn Pro Asn Arg Val Phe
            340                 345                 350
Lys Val Asn Thr Asn Ala Tyr Tyr Glu Met Ser Gly Leu Glu Val Ser
            355                 360                 365
Phe Glu Glu Leu Arg Thr Phe Gly Gly His Asp Ala Lys Phe Ile Asp
            370                 375                 380
Ser Leu Gln Glu Asn Glu Phe Arg Leu Tyr Tyr Tyr Asn Lys Phe Lys
385                 390                 395                 400
Asp Ile Ala Ser Thr Leu Asn Lys Ala Lys Ser Ile Val Gly Thr Thr
                    405                 410                 415
Ala Ser Leu Gln Tyr Met Lys Asn Val Phe Lys Glu Lys Tyr Leu Leu
            420                 425                 430
Ser Glu Asp Thr Ser Gly Lys Phe Ser Val Asp Lys Leu Lys Phe Asp
            435                 440                 445
Lys Leu Tyr Lys Met Leu Thr Glu Ile Tyr Thr Glu Asp Asn Phe Val
            450                 455                 460
Lys Phe Phe Lys Val Leu Asn Arg Lys Thr Tyr Leu Asn Phe Asp Lys
465                 470                 475                 480
Ala Val Phe Lys Ile Asn Ile Val Pro Lys Val Asn Tyr Thr Ile Tyr
                    485                 490                 495
Asp Gly Phe Asn Leu Arg Asn Thr Asn Leu Ala Ala Asn Phe Asn Gly
            500                 505                 510
Gln Asn Thr Glu Ile Asn Asn Met Asn Phe Thr Lys Leu Lys Asn Phe
            515                 520                 525
```

-continued

Thr Gly Leu Phe Glu Phe
        530

<210> SEQ ID NO 12
<211> LENGTH: 1405
<212> TYPE: PRT
<213> ORGANISM: Artificial Sequence
<220> FEATURE:
<223> OTHER INFORMATION: Synthetic

<400> SEQUENCE: 12

Met His His His His His Gly Gly Ser Gly Gly Ser
1               5                   10                  15

Glu Lys Pro Tyr Lys Cys Pro Glu Cys Gly Lys Ser Phe Ser Ala Ser
                20                  25                  30

Ala Ala Leu Val Ala His Gln Arg Thr His Thr Gly Glu Lys Pro Tyr
            35                  40                  45

Lys Cys Pro Glu Cys Gly Lys Ser Phe Ser Ala Ser Ala Ala Leu Val
        50                  55                  60

Ala His Gln Arg Thr His Thr Gly Glu Lys Pro Tyr Lys Cys Pro Glu
65                  70                  75                  80

Cys Gly Lys Ser Phe Ser Ala Ser Ala Ala Leu Val Ala His Gln Arg
                85                  90                  95

Thr His Thr Gly Gly Ser Gly Gly Ser Gly Gly Ser Met Pro Phe
            100                 105                 110

Val Asn Lys Gln Phe Asn Tyr Lys Asp Pro Val Asn Gly Val Asp Ile
        115                 120                 125

Ala Tyr Ile Lys Ile Pro Asn Val Gly Gln Met Gln Pro Val Lys Ala
130                 135                 140

Phe Lys Ile His Asn Lys Ile Trp Val Ile Pro Glu Arg Asp Thr Phe
145                 150                 155                 160

Thr Asn Pro Glu Glu Gly Asp Leu Asn Pro Pro Glu Ala Lys Gln
                165                 170                 175

Val Pro Val Ser Tyr Tyr Asp Ser Thr Tyr Leu Ser Thr Asp Asn Glu
        180                 185                 190

Lys Asp Asn Tyr Leu Lys Gly Val Thr Lys Leu Phe Glu Arg Ile Tyr
    195                 200                 205

Ser Thr Asp Leu Gly Arg Met Leu Leu Thr Ser Ile Val Arg Gly Ile
210                 215                 220

Pro Phe Trp Gly Gly Ser Thr Ile Asp Thr Glu Leu Lys Val Ile Asp
225                 230                 235                 240

Thr Asn Cys Ile Asn Val Ile Gln Pro Asp Gly Ser Tyr Arg Ser Glu
                245                 250                 255

Glu Leu Asn Leu Val Ile Ile Gly Pro Ser Ala Asp Ile Ile Gln Phe
        260                 265                 270

Glu Cys Lys Ser Phe Gly His Glu Val Leu Asn Leu Thr Arg Asn Gly
    275                 280                 285

Tyr Gly Ser Thr Gln Tyr Ile Arg Phe Ser Pro Asp Phe Thr Phe Gly
290                 295                 300

Phe Glu Glu Ser Leu Glu Val Asp Thr Asn Pro Leu Leu Gly Ala Gly
305                 310                 315                 320

Lys Phe Ala Thr Asp Pro Ala Val Thr Leu Ala His Glu Leu Ile His
                325                 330                 335

Ala Gly His Arg Leu Tyr Gly Ile Ala Ile Asn Pro Asn Arg Val Phe
        340                 345                 350

```
Lys Val Asn Thr Asn Ala Tyr Glu Met Ser Gly Leu Glu Val Ser
            355                 360                 365

Phe Glu Glu Leu Arg Thr Phe Gly Gly His Asp Ala Lys Phe Ile Asp
    370                 375                 380

Ser Leu Gln Glu Asn Glu Phe Arg Leu Tyr Tyr Asn Lys Phe Lys
385                 390                 395                 400

Asp Ile Ala Ser Thr Leu Asn Lys Ala Lys Ser Ile Val Gly Thr Thr
                405                 410                 415

Ala Ser Leu Gln Tyr Met Lys Asn Val Phe Lys Glu Lys Tyr Leu Leu
            420                 425                 430

Ser Glu Asp Thr Ser Gly Lys Phe Ser Val Asp Lys Leu Lys Phe Asp
            435                 440                 445

Lys Leu Tyr Lys Met Leu Thr Glu Ile Tyr Thr Glu Asp Asn Phe Val
450                 455                 460

Lys Phe Phe Lys Val Leu Asn Arg Lys Thr Tyr Leu Asn Phe Asp Lys
465                 470                 475                 480

Ala Val Phe Lys Ile Asn Ile Val Pro Lys Val Asn Tyr Thr Ile Tyr
                485                 490                 495

Asp Gly Phe Asn Leu Arg Asn Thr Asn Leu Ala Ala Asn Phe Asn Gly
            500                 505                 510

Gln Asn Thr Glu Ile Asn Asn Met Asn Phe Thr Lys Leu Lys Asn Phe
            515                 520                 525

Thr Gly Leu Phe Glu Phe Tyr Lys Leu Leu Cys Val Arg Gly Ile Ile
            530                 535                 540

Thr Ser Lys Thr Lys Ser Leu Asp Lys Gly Tyr Asn Lys Ala Leu Asn
545                 550                 555                 560

Asp Leu Cys Ile Lys Val Asn Asn Trp Asp Leu Phe Phe Ser Pro Ser
                565                 570                 575

Glu Asp Asn Phe Thr Asn Asp Leu Asn Lys Gly Glu Glu Ile Thr Ser
            580                 585                 590

Asp Thr Asn Ile Glu Ala Ala Glu Glu Asn Ile Ser Leu Asp Leu Ile
            595                 600                 605

Gln Gln Tyr Tyr Leu Thr Phe Asn Phe Asp Asn Glu Pro Glu Asn Ile
            610                 615                 620

Ser Ile Glu Asn Leu Ser Ser Asp Ile Ile Gly Gln Leu Glu Leu Met
625                 630                 635                 640

Pro Asn Ile Glu Arg Phe Pro Asn Gly Lys Lys Tyr Glu Leu Asp Lys
                645                 650                 655

Tyr Thr Met Phe His Tyr Leu Arg Ala Gln Glu Phe Glu His Gly Lys
            660                 665                 670

Ser Arg Ile Ala Leu Thr Asn Ser Val Asn Glu Ala Leu Leu Asn Pro
            675                 680                 685

Ser Arg Val Tyr Thr Phe Phe Ser Ser Asp Tyr Val Lys Lys Val Asn
            690                 695                 700

Lys Ala Thr Glu Ala Ala Met Phe Leu Gly Trp Val Glu Gln Leu Val
705                 710                 715                 720

Tyr Asp Phe Thr Asp Glu Thr Ser Glu Val Ser Thr Thr Asp Lys Ile
                725                 730                 735

Ala Asp Ile Thr Ile Ile Ile Pro Tyr Ile Gly Pro Ala Leu Asn Ile
            740                 745                 750

Gly Asn Met Leu Tyr Lys Asp Asp Phe Val Gly Ala Leu Ile Phe Ser
            755                 760                 765
```

```
Gly Ala Val Ile Leu Leu Glu Phe Ile Pro Glu Ile Ala Ile Pro Val
770                 775                 780

Leu Gly Thr Phe Ala Leu Val Ser Tyr Ile Ala Asn Lys Val Leu Thr
785                 790                 795                 800

Val Gln Thr Ile Asp Asn Ala Leu Ser Lys Arg Asn Glu Lys Trp Asp
            805                 810                 815

Glu Val Tyr Lys Tyr Ile Val Thr Asn Trp Leu Ala Lys Val Asn Thr
            820                 825                 830

Gln Ile Asp Leu Ile Arg Lys Lys Met Lys Glu Ala Leu Glu Asn Gln
            835                 840                 845

Ala Glu Ala Thr Lys Ala Ile Ile Asn Tyr Gln Tyr Asn Gln Tyr Thr
850                 855                 860

Glu Glu Glu Lys Asn Asn Ile Asn Phe Asn Ile Asp Asp Leu Ser Ser
865                 870                 875                 880

Lys Leu Asn Glu Ser Ile Asn Lys Ala Met Ile Asn Ile Asn Lys Phe
                885                 890                 895

Leu Asn Gln Cys Ser Val Ser Tyr Leu Met Asn Ser Met Ile Pro Tyr
            900                 905                 910

Gly Val Lys Arg Leu Glu Asp Phe Asp Ala Ser Leu Lys Asp Ala Leu
            915                 920                 925

Leu Lys Tyr Ile Tyr Asp Asn Arg Gly Thr Leu Ile Gly Gln Val Asp
930                 935                 940

Arg Leu Lys Asp Lys Val Asn Asn Thr Leu Ser Thr Asp Ile Pro Phe
945                 950                 955                 960

Gln Leu Ser Lys Tyr Val Asp Asn Gln Arg Leu Leu Ser Thr Phe Thr
            965                 970                 975

Glu Tyr Ile Lys Asn Ile Ile Asn Thr Ser Ile Leu Asn Leu Arg Tyr
            980                 985                 990

Glu Ser Asn His Leu Ile Asp Leu Ser Arg Tyr Ala Ser Lys Ile Asn
            995                 1000                1005

Ile Gly Ser Lys Val Asn Phe Asp Pro Ile Asp Lys Asn Gln Ile
     1010                1015                1020

Gln Leu Phe Asn Leu Glu Ser Ser Lys Ile Glu Val Ile Leu Lys
     1025                1030                1035

Asn Ala Ile Val Tyr Asn Ser Met Tyr Glu Asn Phe Ser Thr Ser
     1040                1045                1050

Phe Trp Ile Arg Ile Pro Lys Tyr Phe Asn Ser Ile Ser Leu Asn
     1055                1060                1065

Asn Glu Tyr Thr Ile Ile Asn Cys Met Glu Asn Asn Ser Gly Trp
     1070                1075                1080

Lys Val Ser Leu Asn Tyr Gly Glu Ile Ile Trp Thr Leu Gln Asp
     1085                1090                1095

Thr Gln Glu Ile Lys Gln Arg Val Val Phe Lys Tyr Ser Gln Met
     1100                1105                1110

Ile Asn Ile Ser Asp Tyr Ile Asn Arg Trp Ile Phe Val Thr Ile
     1115                1120                1125

Thr Asn Asn Arg Leu Asn Asn Ser Lys Ile Tyr Ile Asn Gly Arg
     1130                1135                1140

Leu Ile Asp Gln Lys Pro Ile Ser Asn Leu Gly Asn Ile His Ala
     1145                1150                1155

Ser Asn Asn Ile Met Phe Lys Leu Asp Gly Cys Arg Asp Thr His
     1160                1165                1170

Arg Tyr Ile Trp Ile Lys Tyr Phe Asn Leu Phe Asp Lys Glu Leu
```

```
            1175                1180                1185

Asn Glu Lys Glu Ile Lys Asp Leu Tyr Asp Asn Gln Ser Asn Ser
    1190                1195                1200

Gly Ile Leu Lys Asp Phe Trp Gly Asp Tyr Leu Gln Tyr Asp Lys
    1205                1210                1215

Pro Tyr Tyr Met Leu Asn Leu Tyr Asp Pro Asn Lys Tyr Val Asp
    1220                1225                1230

Val Asn Asn Val Gly Ile Arg Gly Tyr Met Tyr Leu Lys Gly Pro
    1235                1240                1245

Arg Gly Ser Val Met Thr Thr Asn Ile Tyr Leu Asn Ser Ser Leu
    1250                1255                1260

Tyr Arg Gly Thr Lys Phe Ile Ile Lys Lys Tyr Ala Ser Gly Asn
    1265                1270                1275

Lys Asp Asn Ile Val Arg Asn Asp Arg Val Tyr Ile Asn Val
    1280                1285                1290

Val Val Lys Asn Lys Glu Tyr Arg Leu Ala Thr Asn Ala Ser Gln
    1295                1300                1305

Ala Gly Val Glu Lys Ile Leu Ser Ala Leu Glu Ile Pro Asp Val
    1310                1315                1320

Gly Asn Leu Ser Gln Val Val Met Lys Ser Lys Asn Asp Gln
    1325                1330                1335

Gly Ile Thr Asn Lys Cys Lys Met Asn Leu Gln Asp Asn Asn Gly
    1340                1345                1350

Asn Asp Ile Gly Phe Ile Gly Phe His Gln Phe Asn Asn Ile Ala
    1355                1360                1365

Lys Leu Val Ala Ser Asn Trp Tyr Asn Arg Gln Ile Glu Arg Ser
    1370                1375                1380

Ser Arg Thr Leu Gly Cys Ser Trp Glu Phe Ile Pro Val Asp Asp
    1385                1390                1395

Gly Trp Gly Glu Arg Pro Leu
    1400                1405

<210> SEQ ID NO 13
<211> LENGTH: 533
<212> TYPE: PRT
<213> ORGANISM: Artificial Sequence
<220> FEATURE:
<223> OTHER INFORMATION: Synthetic

<400> SEQUENCE: 13

Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Glu
        50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
```

```
            115                 120                 125
Val Ile Asp Thr Asn Cys Ile Asn Val Ile Gln Pro Asp Gly Ser Tyr
130                 135                 140

Arg Ser Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                    165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
        210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
                260                 265                 270

Phe Ile Asp Ser Leu Gln Glu Asn Glu Phe Arg Leu Tyr Tyr Asn
                275                 280                 285

Lys Phe Lys Asp Ile Ala Ser Thr Leu Asn Lys Ala Lys Ser Ile Val
                290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                    325                 330                 335

Lys Phe Asp Lys Leu Tyr Lys Met Leu Thr Glu Ile Tyr Thr Glu Asp
                340                 345                 350

Asn Phe Val Lys Phe Phe Lys Val Leu Asn Arg Lys Thr Tyr Leu Asn
                    355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                    405                 410                 415

Lys Asn Phe Thr Gly Leu Phe Glu Phe Gly Ser Gly Gly Ser Gly
                420                 425                 430

Gly Ser Glu Lys Pro Tyr Lys Cys Pro Glu Cys Gly Lys Ser Phe Ser
        435                 440                 445

Ala Ser Ala Ala Leu Val Ala His Gln Arg Thr His Thr Gly Glu Lys
    450                 455                 460

Pro Tyr Lys Cys Pro Glu Cys Gly Lys Ser Phe Ser Ala Ser Ala Ala
465                 470                 475                 480

Leu Val Ala His Gln Arg Thr His Thr Gly Glu Lys Pro Tyr Lys Cys
                485                 490                 495

Pro Glu Cys Gly Lys Ser Phe Ser Ala Ser Ala Ala Leu Val Ala His
            500                 505                 510

Gln Arg Thr His Thr Gly Gly Ser Gly Gly Ser Gly Gly Ser His
        515                 520                 525

His His His His
    530
```

<210> SEQ ID NO 14
<211> LENGTH: 1404
<212> TYPE: PRT
<213> ORGANISM: Artificial Sequence
<220> FEATURE:
<223> OTHER INFORMATION: Synthetic

<400> SEQUENCE: 14

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Val Gly Gln Met Gln Pro
                 20                  25                  30

Val Lys Ala Phe Lys Ile His Asn Lys Ile Trp Val Ile Pro Glu Arg
             35                  40                  45

Asp Thr Phe Thr Asn Pro Glu Glu Gly Asp Leu Asn Pro Pro Pro Glu
         50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
        130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365
```

```
Phe Asp Lys Ala Val Phe Lys Ile Asn Ile Val Pro Lys Val Asn Tyr
        370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Lys Gly Tyr Asn Lys
                435                 440                 445

Ala Leu Asn Asp Leu Cys Ile Lys Val Asn Asn Trp Asp Leu Phe Phe
        450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Asn Ile Ser Leu
                485                 490                 495

Asp Leu Ile Gln Gln Tyr Tyr Leu Thr Phe Asn Phe Asp Asn Glu Pro
                500                 505                 510

Glu Asn Ile Ser Ile Glu Asn Leu Ser Ser Asp Ile Ile Gly Gln Leu
                515                 520                 525

Glu Leu Met Pro Asn Ile Glu Arg Phe Pro Asn Gly Lys Lys Tyr Glu
        530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
                580                 585                 590

Lys Val Asn Lys Ala Thr Glu Ala Ala Met Phe Leu Gly Trp Val Glu
                595                 600                 605

Gln Leu Val Tyr Asp Phe Thr Asp Glu Thr Ser Glu Val Ser Thr Thr
        610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
                660                 665                 670

Ile Pro Val Leu Gly Thr Phe Ala Leu Val Ser Tyr Ile Ala Asn Lys
                675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
                740                 745                 750

Gln Tyr Thr Glu Glu Glu Lys Asn Asn Ile Asn Phe Asn Ile Asp Asp
                755                 760                 765

Leu Ser Ser Lys Leu Asn Glu Ser Ile Asn Lys Ala Met Ile Asn Ile
        770                 775                 780
```

-continued

```
Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
        820                 825                 830

Gln Val Asp Arg Leu Lys Asp Lys Val Asn Asn Thr Leu Ser Thr Asp
        835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
        995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185

Lys Glu Tyr Arg Leu Ala Thr Asn Ala Ser Gln Ala Gly Val Glu
```

```
                1190                1195                1200
Lys  Ile  Leu  Ser  Ala  Leu  Glu  Ile  Pro  Asp  Val  Gly  Asn  Leu  Ser
           1205                1210                1215

Gln  Val  Val  Met  Lys  Ser  Lys  Asn  Asp  Gln  Gly  Ile  Thr  Asn
1220                1225                1230

Lys  Cys  Lys  Met  Asn  Leu  Gln  Asp  Asn  Asn  Gly  Asn  Asp  Ile  Gly
     1235                1240                1245

Phe  Ile  Gly  Phe  His  Gln  Phe  Asn  Asn  Ile  Ala  Lys  Leu  Val  Ala
1250                1255                1260

Ser  Asn  Trp  Tyr  Asn  Arg  Gln  Ile  Glu  Arg  Ser  Arg  Thr  Leu
1265                1270                1275

Gly  Cys  Ser  Trp  Glu  Phe  Ile  Pro  Val  Asp  Asp  Gly  Trp  Gly  Glu
     1280                1285                1290

Arg  Pro  Leu  Gly  Gly  Ser  Gly  Ser  Gly  Gly  Ser  Glu  Lys  Pro
1295                1300                1305

Tyr  Lys  Cys  Pro  Glu  Cys  Gly  Lys  Ser  Phe  Ser  Ala  Ser  Ala  Ala
     1310                1315                1320

Leu  Val  Ala  His  Gln  Arg  Thr  His  Thr  Gly  Glu  Lys  Pro  Tyr  Lys
1325                1330                1335

Cys  Pro  Glu  Cys  Gly  Lys  Ser  Phe  Ser  Ala  Ser  Ala  Ala  Leu  Val
     1340                1345                1350

Ala  His  Gln  Arg  Thr  His  Thr  Gly  Glu  Lys  Pro  Tyr  Lys  Cys  Pro
1355                1360                1365

Glu  Cys  Gly  Lys  Ser  Phe  Ser  Ala  Ser  Ala  Ala  Leu  Val  Ala  His
     1370                1375                1380

Gln  Arg  Thr  His  Thr  Gly  Gly  Gly  Ser  Gly  Gly  Ser  Gly  Gly  Ser
1385                1390                1395

His  His  His  His  His  His
     1400

<210> SEQ ID NO 15
<211> LENGTH: 1498
<212> TYPE: PRT
<213> ORGANISM: Artificial Sequence
<220> FEATURE:
<223> OTHER INFORMATION: Synthetic

<400> SEQUENCE: 15

Met  His  His  His  His  His  Gly  Gly  Ser  Gly  Gly  Ser  Gly  Gly  Ser
1                  5                  10                 15

Glu  Lys  Pro  Tyr  Lys  Cys  Pro  Glu  Cys  Gly  Lys  Ser  Phe  Ser  Ala  Ser
                20                  25                  30

Ala  Ala  Leu  Val  Ala  His  Gln  Arg  Thr  His  Thr  Gly  Glu  Lys  Pro  Tyr
            35                  40                  45

Lys  Cys  Pro  Glu  Cys  Gly  Lys  Ser  Phe  Ser  Ala  Ser  Ala  Ala  Leu  Val
        50                  55                  60

Ala  His  Gln  Arg  Thr  His  Thr  Gly  Glu  Lys  Pro  Tyr  Lys  Cys  Pro  Glu
65                  70                  75                  80

Cys  Gly  Lys  Ser  Phe  Ser  Ala  Ser  Ala  Ala  Leu  Val  Ala  His  Gln  Arg
                85                  90                  95

Thr  His  Thr  Gly  Gly  Gly  Ser  Gly  Gly  Ser  Gly  Gly  Ser  Met  Pro  Phe
            100                 105                 110

Val  Asn  Lys  Gln  Phe  Asn  Tyr  Lys  Asp  Pro  Val  Asn  Gly  Val  Asp  Ile
        115                 120                 125

Ala  Tyr  Ile  Lys  Ile  Pro  Asn  Val  Gly  Gln  Met  Gln  Pro  Val  Lys  Ala
```

```
                130                 135                 140
Phe Lys Ile His Asn Lys Ile Trp Val Ile Pro Glu Arg Asp Thr Phe
145                 150                 155                 160

Thr Asn Pro Glu Glu Gly Asp Leu Asn Pro Pro Glu Ala Lys Gln
                165                 170                 175

Val Pro Val Ser Tyr Tyr Asp Ser Thr Tyr Leu Ser Thr Asp Asn Glu
                180                 185                 190

Lys Asp Asn Tyr Leu Lys Gly Val Thr Lys Leu Phe Glu Arg Ile Tyr
                195                 200                 205

Ser Thr Asp Leu Gly Arg Met Leu Leu Thr Ser Ile Val Arg Gly Ile
                210                 215                 220

Pro Phe Trp Gly Gly Ser Thr Ile Asp Thr Glu Leu Lys Val Ile Asp
225                 230                 235                 240

Thr Asn Cys Ile Asn Val Ile Gln Pro Asp Gly Ser Tyr Arg Ser Glu
                245                 250                 255

Glu Leu Asn Leu Val Ile Ile Gly Pro Ser Ala Asp Ile Ile Gln Phe
                260                 265                 270

Glu Cys Lys Ser Phe Gly His Glu Val Leu Asn Leu Thr Arg Asn Gly
                275                 280                 285

Tyr Gly Ser Thr Gln Tyr Ile Arg Phe Ser Pro Asp Phe Thr Phe Gly
                290                 295                 300

Phe Glu Glu Ser Leu Glu Val Asp Thr Asn Pro Leu Leu Gly Ala Gly
305                 310                 315                 320

Lys Phe Ala Thr Asp Pro Ala Val Thr Leu Ala His Glu Leu Ile His
                325                 330                 335

Ala Gly His Arg Leu Tyr Gly Ile Ala Ile Asn Pro Asn Arg Val Phe
                340                 345                 350

Lys Val Asn Thr Asn Ala Tyr Tyr Glu Met Ser Gly Leu Glu Val Ser
                355                 360                 365

Phe Glu Glu Leu Arg Thr Phe Gly Gly His Asp Ala Lys Phe Ile Asp
                370                 375                 380

Ser Leu Gln Glu Asn Glu Phe Arg Leu Tyr Tyr Tyr Asn Lys Phe Lys
385                 390                 395                 400

Asp Ile Ala Ser Thr Leu Asn Lys Ala Lys Ser Ile Val Gly Thr Thr
                405                 410                 415

Ala Ser Leu Gln Tyr Met Lys Asn Val Phe Lys Glu Lys Tyr Leu Leu
                420                 425                 430

Ser Glu Asp Thr Ser Gly Lys Phe Ser Val Asp Lys Leu Lys Phe Asp
                435                 440                 445

Lys Leu Tyr Lys Met Leu Thr Glu Ile Tyr Thr Glu Asp Asn Phe Val
                450                 455                 460

Lys Phe Phe Lys Val Leu Asn Arg Lys Thr Tyr Leu Asn Phe Asp Lys
465                 470                 475                 480

Ala Val Phe Lys Ile Asn Ile Val Pro Lys Val Asn Tyr Thr Ile Tyr
                485                 490                 495

Asp Gly Phe Asn Leu Arg Asn Thr Asn Leu Ala Ala Asn Phe Asn Gly
                500                 505                 510

Gln Asn Thr Glu Ile Asn Asn Met Asn Phe Thr Lys Leu Lys Asn Phe
                515                 520                 525

Thr Gly Leu Phe Glu Phe Tyr Lys Leu Leu Cys Val Arg Gly Ile Ile
                530                 535                 540

Thr Ser Lys Thr Lys Ser Leu Asp Lys Gly Tyr Asn Lys Ala Leu Asn
545                 550                 555                 560
```

-continued

```
Asp Leu Cys Ile Lys Val Asn Trp Asp Leu Phe Ser Pro Ser
            565                 570                 575

Glu Asp Asn Phe Thr Asn Asp Leu Asn Lys Gly Glu Glu Ile Thr Ser
        580                 585                 590

Asp Thr Asn Ile Glu Ala Ala Glu Glu Asn Ile Ser Leu Asp Leu Ile
        595                 600                 605

Gln Gln Tyr Tyr Leu Thr Phe Asn Phe Asp Asn Glu Pro Glu Asn Ile
    610                 615                 620

Ser Ile Glu Asn Leu Ser Ser Asp Ile Ile Gly Gln Leu Glu Leu Met
625                 630                 635                 640

Pro Asn Ile Glu Arg Phe Pro Asn Gly Lys Lys Tyr Glu Leu Asp Lys
                645                 650                 655

Tyr Thr Met Phe His Tyr Leu Arg Ala Gln Glu Phe Glu His Gly Lys
            660                 665                 670

Ser Arg Ile Ala Leu Thr Asn Ser Val Asn Glu Ala Leu Leu Asn Pro
        675                 680                 685

Ser Arg Val Tyr Thr Phe Phe Ser Ser Asp Tyr Val Lys Lys Val Asn
    690                 695                 700

Lys Ala Thr Glu Ala Ala Met Phe Leu Gly Trp Val Glu Gln Leu Val
705                 710                 715                 720

Tyr Asp Phe Thr Asp Glu Thr Ser Glu Val Ser Thr Thr Asp Lys Ile
                725                 730                 735

Ala Asp Ile Thr Ile Ile Ile Pro Tyr Ile Gly Pro Ala Leu Asn Ile
            740                 745                 750

Gly Asn Met Leu Tyr Lys Asp Asp Phe Val Gly Ala Leu Ile Phe Ser
        755                 760                 765

Gly Ala Val Ile Leu Leu Glu Phe Ile Pro Glu Ile Ala Ile Pro Val
    770                 775                 780

Leu Gly Thr Phe Ala Leu Val Ser Tyr Ile Ala Asn Lys Val Leu Thr
785                 790                 795                 800

Val Gln Thr Ile Asp Asn Ala Leu Ser Lys Arg Asn Glu Lys Trp Asp
                805                 810                 815

Glu Val Tyr Lys Tyr Ile Val Thr Asn Trp Leu Ala Lys Val Asn Thr
            820                 825                 830

Gln Ile Asp Leu Ile Arg Lys Lys Met Lys Glu Ala Leu Glu Asn Gln
        835                 840                 845

Ala Glu Ala Thr Lys Ala Ile Ile Asn Tyr Gln Tyr Asn Gln Tyr Thr
    850                 855                 860

Glu Glu Glu Lys Asn Asn Ile Asn Phe Asn Ile Asp Asp Leu Ser Ser
865                 870                 875                 880

Lys Leu Asn Glu Ser Ile Asn Lys Ala Met Ile Asn Ile Asn Lys Phe
                885                 890                 895

Leu Asn Gln Cys Ser Val Ser Tyr Leu Met Asn Ser Met Ile Pro Tyr
            900                 905                 910

Gly Val Lys Arg Leu Glu Asp Phe Asp Ala Ser Leu Lys Asp Ala Leu
        915                 920                 925

Leu Lys Tyr Ile Tyr Asp Asn Arg Gly Thr Leu Ile Gly Gln Val Asp
    930                 935                 940

Arg Leu Lys Asp Lys Val Asn Asn Thr Leu Ser Thr Asp Ile Pro Phe
945                 950                 955                 960

Gln Leu Ser Lys Tyr Val Asp Asn Gln Arg Leu Leu Ser Thr Phe Thr
                965                 970                 975
```

-continued

Glu Tyr Ile Lys Asn Ile Ile Asn Thr Ser Ile Leu Asn Leu Arg Tyr
            980                 985                 990

Glu Ser Asn His Leu Ile Asp Leu Ser Arg Tyr Ala Ser Lys Ile Asn
            995                1000                1005

Ile Gly Ser Lys Val Asn Phe Asp Pro Ile Asp Lys Asn Gln Ile
        1010                1015                1020

Gln Leu Phe Asn Leu Glu Ser Ser Lys Ile Glu Val Ile Leu Lys
        1025                1030                1035

Asn Ala Ile Val Tyr Asn Ser Met Tyr Glu Asn Phe Ser Thr Ser
        1040                1045                1050

Phe Trp Ile Arg Ile Pro Lys Tyr Phe Asn Ser Ile Ser Leu Asn
        1055                1060                1065

Asn Glu Tyr Thr Ile Ile Asn Cys Met Glu Asn Asn Ser Gly Trp
        1070                1075                1080

Lys Val Ser Leu Asn Tyr Gly Glu Ile Ile Trp Thr Leu Gln Asp
        1085                1090                1095

Thr Gln Glu Ile Lys Gln Arg Val Val Phe Lys Tyr Ser Gln Met
        1100                1105                1110

Ile Asn Ile Ser Asp Tyr Ile Asn Arg Trp Ile Phe Val Thr Ile
        1115                1120                1125

Thr Asn Asn Arg Leu Asn Asn Ser Lys Ile Tyr Ile Asn Gly Arg
        1130                1135                1140

Leu Ile Asp Gln Lys Pro Ile Ser Asn Leu Gly Asn Ile His Ala
        1145                1150                1155

Ser Asn Asn Ile Met Phe Lys Leu Asp Gly Cys Arg Asp Thr His
        1160                1165                1170

Arg Tyr Ile Trp Ile Lys Tyr Phe Asn Leu Phe Asp Lys Glu Leu
        1175                1180                1185

Asn Glu Lys Glu Ile Lys Asp Leu Tyr Asp Asn Gln Ser Asn Ser
        1190                1195                1200

Gly Ile Leu Lys Asp Phe Trp Gly Asp Tyr Leu Gln Tyr Asp Lys
        1205                1210                1215

Pro Tyr Tyr Met Leu Asn Leu Tyr Asp Pro Asn Lys Tyr Val Asp
        1220                1225                1230

Val Asn Asn Val Gly Ile Arg Gly Tyr Met Tyr Leu Lys Gly Pro
        1235                1240                1245

Arg Gly Ser Val Met Thr Thr Asn Ile Tyr Leu Asn Ser Ser Leu
        1250                1255                1260

Tyr Arg Gly Thr Lys Phe Ile Ile Lys Lys Tyr Ala Ser Gly Asn
        1265                1270                1275

Lys Asp Asn Ile Val Arg Asn Asn Asp Arg Val Tyr Ile Asn Val
        1280                1285                1290

Val Val Lys Asn Lys Glu Tyr Arg Leu Ala Thr Asn Ala Ser Gln
        1295                1300                1305

Ala Gly Val Glu Lys Ile Leu Ser Ala Leu Glu Ile Pro Asp Val
        1310                1315                1320

Gly Asn Leu Ser Gln Val Val Met Lys Ser Lys Asn Asp Gln
        1325                1330                1335

Gly Ile Thr Asn Lys Cys Lys Met Asn Leu Gln Asp Asn Asn Gly
        1340                1345                1350

Asn Asp Ile Gly Phe Ile Gly Phe His Gln Phe Asn Asn Ile Ala
        1355                1360                1365

Lys Leu Val Ala Ser Asn Trp Tyr Asn Arg Gln Ile Glu Arg Ser

-continued

```
              1370                1375                1380

Ser Arg Thr Leu Gly Cys Ser Trp Glu Phe Ile Pro Val Asp Asp
    1385                1390                1395

Gly Trp Gly Glu Arg Pro Leu Gly Gly Ser Gly Gly Ser Gly Gly
    1400                1405                1410

Ser Glu Lys Pro Tyr Lys Cys Pro Glu Cys Gly Lys Ser Phe Ser
    1415                1420                1425

Ala Ser Ala Ala Leu Val Ala His Gln Arg Thr His Thr Gly Glu
    1430                1435                1440

Lys Pro Tyr Lys Cys Pro Glu Cys Gly Lys Ser Phe Ser Ala Ser
    1445                1450                1455

Ala Ala Leu Val Ala His Gln Arg Thr His Thr Gly Glu Lys Pro
    1460                1465                1470

Tyr Lys Cys Pro Glu Cys Gly Lys Ser Phe Ser Ala Ser Ala Ala
    1475                1480                1485

Leu Val Ala His Gln Arg Thr His Thr Gly
    1490                1495

<210> SEQ ID NO 16
<211> LENGTH: 1333
<212> TYPE: PRT
<213> ORGANISM: Artificial Sequence
<220> FEATURE:
<223> OTHER INFORMATION: Synthetic

<400> SEQUENCE: 16

Met His His His His His Gly Gly Ser Gly Gly Ser Gly Gly Ser
1               5                   10                  15

Gly Arg Lys Lys Arg Arg Gln Arg Arg Pro Gln Gly Gly Ser Gly
                20                  25                  30

Gly Ser Gly Gly Ser Met Pro Phe Val Asn Lys Gln Phe Asn Tyr Lys
            35                  40                  45

Asp Pro Val Asn Gly Val Asp Ile Ala Tyr Ile Lys Ile Pro Asn Val
        50                  55                  60

Gly Gln Met Gln Pro Val Lys Ala Phe Lys Ile His Asn Lys Ile Trp
65                  70                  75                  80

Val Ile Pro Glu Arg Asp Thr Phe Thr Asn Pro Glu Glu Gly Asp Leu
                85                  90                  95

Asn Pro Pro Pro Glu Ala Lys Gln Val Pro Val Ser Tyr Tyr Asp Ser
            100                 105                 110

Thr Tyr Leu Ser Thr Asp Asn Glu Lys Asp Asn Tyr Leu Lys Gly Val
        115                 120                 125

Thr Lys Leu Phe Glu Arg Ile Tyr Ser Thr Asp Leu Gly Arg Met Leu
    130                 135                 140

Leu Thr Ser Ile Val Arg Gly Ile Pro Phe Trp Gly Gly Ser Thr Ile
145                 150                 155                 160

Asp Thr Glu Leu Lys Val Ile Asp Thr Asn Cys Ile Asn Val Ile Gln
                165                 170                 175

Pro Asp Gly Ser Tyr Arg Ser Glu Glu Leu Asn Leu Val Ile Ile Gly
            180                 185                 190

Pro Ser Ala Asp Ile Ile Gln Phe Glu Cys Lys Ser Phe Gly His Glu
        195                 200                 205

Val Leu Asn Leu Thr Arg Asn Gly Tyr Gly Ser Thr Gln Tyr Ile Arg
    210                 215                 220

Phe Ser Pro Asp Phe Thr Phe Gly Phe Glu Glu Ser Leu Glu Val Asp
```

```
              225                 230                 235                 240
        Thr Asn Pro Leu Leu Gly Ala Gly Lys Phe Ala Thr Asp Pro Ala Val
                        245                 250                 255

Thr Leu Ala His Glu Leu Ile His Ala Gly His Arg Leu Tyr Gly Ile
                    260                 265                 270

Ala Ile Asn Pro Asn Arg Val Phe Lys Val Asn Thr Asn Ala Tyr Tyr
                    275                 280                 285

Glu Met Ser Gly Leu Glu Val Ser Phe Glu Glu Leu Arg Thr Phe Gly
                290                 295                 300

Gly His Asp Ala Lys Phe Ile Asp Ser Leu Gln Glu Asn Glu Phe Arg
        305                 310                 315                 320

Leu Tyr Tyr Tyr Asn Lys Phe Lys Asp Ile Ala Ser Thr Leu Asn Lys
                        325                 330                 335

Ala Lys Ser Ile Val Gly Thr Thr Ala Ser Leu Gln Tyr Met Lys Asn
                    340                 345                 350

Val Phe Lys Glu Lys Tyr Leu Leu Ser Glu Asp Thr Ser Gly Lys Phe
                    355                 360                 365

Ser Val Asp Lys Leu Lys Phe Asp Lys Leu Tyr Lys Met Leu Thr Glu
                370                 375                 380

Ile Tyr Thr Glu Asp Asn Phe Val Lys Phe Phe Lys Val Leu Asn Arg
        385                 390                 395                 400

Lys Thr Tyr Leu Asn Phe Asp Lys Ala Val Phe Lys Ile Asn Ile Val
                        405                 410                 415

Pro Lys Val Asn Tyr Thr Ile Tyr Asp Gly Phe Asn Leu Arg Asn Thr
                    420                 425                 430

Asn Leu Ala Ala Asn Phe Asn Gly Gln Asn Thr Glu Ile Asn Asn Met
                    435                 440                 445

Asn Phe Thr Lys Leu Lys Asn Phe Thr Gly Leu Phe Glu Phe Tyr Lys
                450                 455                 460

Leu Leu Cys Val Arg Gly Ile Ile Thr Ser Lys Thr Lys Ser Leu Asp
        465                 470                 475                 480

Lys Gly Tyr Asn Lys Ala Leu Asn Asp Leu Cys Ile Lys Val Asn Asn
                        485                 490                 495

Trp Asp Leu Phe Phe Ser Pro Ser Glu Asp Asn Phe Thr Asn Asp Leu
                    500                 505                 510

Asn Lys Gly Glu Glu Ile Thr Ser Asp Thr Asn Ile Glu Ala Ala Glu
                    515                 520                 525

Glu Asn Ile Ser Leu Asp Leu Ile Gln Gln Tyr Tyr Leu Thr Phe Asn
                530                 535                 540

Phe Asp Asn Glu Pro Glu Asn Ile Ser Ile Glu Asn Leu Ser Ser Asp
        545                 550                 555                 560

Ile Ile Gly Gln Leu Glu Leu Met Pro Asn Ile Glu Arg Phe Pro Asn
                        565                 570                 575

Gly Lys Lys Tyr Glu Leu Asp Lys Tyr Thr Met Phe His Tyr Leu Arg
                    580                 585                 590

Ala Gln Glu Phe Glu His Gly Lys Ser Arg Ile Ala Leu Thr Asn Ser
                    595                 600                 605

Val Asn Glu Ala Leu Leu Asn Pro Ser Arg Val Tyr Thr Phe Phe Ser
                610                 615                 620

Ser Asp Tyr Val Lys Lys Val Asn Lys Ala Thr Glu Ala Ala Met Phe
        625                 630                 635                 640

Leu Gly Trp Val Glu Gln Leu Val Tyr Asp Phe Thr Asp Glu Thr Ser
                        645                 650                 655
```

-continued

```
Glu Val Ser Thr Thr Asp Lys Ile Ala Asp Ile Thr Ile Ile Ile Pro
                660                 665                 670

Tyr Ile Gly Pro Ala Leu Asn Ile Gly Asn Met Leu Tyr Lys Asp Asp
        675                 680                 685

Phe Val Gly Ala Leu Ile Phe Ser Gly Ala Val Ile Leu Leu Glu Phe
    690                 695                 700

Ile Pro Glu Ile Ala Ile Pro Val Leu Gly Thr Phe Ala Leu Val Ser
705                 710                 715                 720

Tyr Ile Ala Asn Lys Val Leu Thr Val Gln Thr Ile Asp Asn Ala Leu
                725                 730                 735

Ser Lys Arg Asn Glu Lys Trp Asp Glu Val Tyr Lys Tyr Ile Val Thr
        740                 745                 750

Asn Trp Leu Ala Lys Val Asn Thr Gln Ile Asp Leu Ile Arg Lys Lys
    755                 760                 765

Met Lys Glu Ala Leu Glu Asn Gln Ala Glu Ala Thr Lys Ala Ile Ile
770                 775                 780

Asn Tyr Gln Tyr Asn Gln Tyr Thr Glu Glu Lys Asn Asn Ile Asn
785                 790                 795                 800

Phe Asn Ile Asp Asp Leu Ser Ser Lys Leu Asn Glu Ser Ile Asn Lys
                805                 810                 815

Ala Met Ile Asn Ile Asn Lys Phe Leu Asn Gln Cys Ser Val Ser Tyr
        820                 825                 830

Leu Met Asn Ser Met Ile Pro Tyr Gly Val Lys Arg Leu Glu Asp Phe
    835                 840                 845

Asp Ala Ser Leu Lys Asp Ala Leu Leu Lys Tyr Ile Tyr Asp Asn Arg
850                 855                 860

Gly Thr Leu Ile Gly Gln Val Asp Arg Leu Lys Asp Lys Val Asn Asn
865                 870                 875                 880

Thr Leu Ser Thr Asp Ile Pro Phe Gln Leu Ser Lys Tyr Val Asp Asn
                885                 890                 895

Gln Arg Leu Leu Ser Thr Phe Thr Glu Tyr Ile Lys Asn Ile Ile Asn
        900                 905                 910

Thr Ser Ile Leu Asn Leu Arg Tyr Glu Ser Asn His Leu Ile Asp Leu
    915                 920                 925

Ser Arg Tyr Ala Ser Lys Ile Asn Ile Gly Ser Lys Val Asn Phe Asp
930                 935                 940

Pro Ile Asp Lys Asn Gln Ile Gln Leu Phe Asn Leu Glu Ser Ser Lys
945                 950                 955                 960

Ile Glu Val Ile Leu Lys Asn Ala Ile Val Tyr Asn Ser Met Tyr Glu
                965                 970                 975

Asn Phe Ser Thr Ser Phe Trp Ile Arg Ile Pro Lys Tyr Phe Asn Ser
        980                 985                 990

Ile Ser Leu Asn Asn Glu Tyr Thr Ile Ile Asn Cys Met Glu Asn Asn
    995                 1000                1005

Ser Gly Trp Lys Val Ser Leu Asn Tyr Gly Glu Ile Ile Trp Thr
        1010                1015                1020

Leu Gln Asp Thr Gln Glu Ile Lys Gln Arg Val Val Phe Lys Tyr
        1025                1030                1035

Ser Gln Met Ile Asn Ile Ser Asp Tyr Ile Asn Arg Trp Ile Phe
        1040                1045                1050

Val Thr Ile Thr Asn Asn Arg Leu Asn Asn Ser Lys Ile Tyr Ile
        1055                1060                1065
```

```
Asn Gly Arg Leu Ile Asp Gln Lys Pro Ile Ser Asn Leu Gly Asn
    1070                1075                1080

Ile His Ala Ser Asn Asn Ile Met Phe Lys Leu Asp Gly Cys Arg
    1085                1090                1095

Asp Thr His Arg Tyr Ile Trp Ile Lys Tyr Phe Asn Leu Phe Asp
    1100                1105                1110

Lys Glu Leu Asn Glu Lys Glu Ile Lys Asp Leu Tyr Asp Asn Gln
    1115                1120                1125

Ser Asn Ser Gly Ile Leu Lys Asp Phe Trp Gly Asp Tyr Leu Gln
    1130                1135                1140

Tyr Asp Lys Pro Tyr Tyr Met Leu Asn Leu Tyr Asp Pro Asn Lys
    1145                1150                1155

Tyr Val Asp Val Asn Asn Val Gly Ile Arg Gly Tyr Met Tyr Leu
    1160                1165                1170

Lys Gly Pro Arg Gly Ser Val Met Thr Thr Asn Ile Tyr Leu Asn
    1175                1180                1185

Ser Ser Leu Tyr Arg Gly Thr Lys Phe Ile Ile Lys Lys Tyr Ala
    1190                1195                1200

Ser Gly Asn Lys Asp Asn Ile Val Arg Asn Asn Asp Arg Val Tyr
    1205                1210                1215

Ile Asn Val Val Val Lys Asn Lys Glu Tyr Arg Leu Ala Thr Asn
    1220                1225                1230

Ala Ser Gln Ala Gly Val Glu Lys Ile Leu Ser Ala Leu Glu Ile
    1235                1240                1245

Pro Asp Val Gly Asn Leu Ser Gln Val Val Met Lys Ser Lys
    1250                1255                1260

Asn Asp Gln Gly Ile Thr Asn Lys Cys Lys Met Asn Leu Gln Asp
    1265                1270                1275

Asn Asn Gly Asn Asp Ile Gly Phe Ile Gly Phe His Gln Phe Asn
    1280                1285                1290

Asn Ile Ala Lys Leu Val Ala Ser Asn Trp Tyr Asn Arg Gln Ile
    1295                1300                1305

Glu Arg Ser Ser Arg Thr Leu Gly Cys Ser Trp Glu Phe Ile Pro
    1310                1315                1320

Val Asp Asp Gly Trp Gly Glu Arg Pro Leu
    1325                1330

<210> SEQ ID NO 17
<211> LENGTH: 1342
<212> TYPE: PRT
<213> ORGANISM: Artificial Sequence
<220> FEATURE:
<223> OTHER INFORMATION: Synthetic

<400> SEQUENCE: 17

Met His His His His His Gly Gly Ser Gly Gly Ser Gly Gly Ser
1               5                   10                  15

Lys Glu Thr Trp Trp Glu Thr Trp Trp Thr Glu Trp Ser Gln Pro Lys
                20                  25                  30

Lys Lys Arg Lys Val Gly Gly Ser Gly Gly Ser Gly Gly Ser Met Pro
            35                  40                  45

Phe Val Asn Lys Gln Phe Asn Tyr Lys Asp Pro Val Asn Gly Val Asp
        50                  55                  60

Ile Ala Tyr Ile Lys Ile Pro Asn Val Gly Gln Met Gln Pro Val Lys
65                  70                  75                  80
```

```
Ala Phe Lys Ile His Asn Lys Ile Trp Val Ile Pro Glu Arg Asp Thr
                85                  90                  95

Phe Thr Asn Pro Glu Glu Gly Asp Leu Asn Pro Pro Glu Ala Lys
            100                 105                 110

Gln Val Pro Val Ser Tyr Tyr Asp Ser Thr Tyr Leu Ser Thr Asp Asn
            115                 120                 125

Glu Lys Asp Asn Tyr Leu Lys Gly Val Thr Lys Leu Phe Glu Arg Ile
        130                 135                 140

Tyr Ser Thr Asp Leu Gly Arg Met Leu Leu Thr Ser Ile Val Arg Gly
145                 150                 155                 160

Ile Pro Phe Trp Gly Gly Ser Thr Ile Asp Thr Glu Leu Lys Val Ile
                165                 170                 175

Asp Thr Asn Cys Ile Asn Val Ile Gln Pro Asp Gly Ser Tyr Arg Ser
            180                 185                 190

Glu Glu Leu Asn Leu Val Ile Ile Gly Pro Ser Ala Asp Ile Ile Gln
        195                 200                 205

Phe Glu Cys Lys Ser Phe Gly His Glu Val Leu Asn Leu Thr Arg Asn
210                 215                 220

Gly Tyr Gly Ser Thr Gln Tyr Ile Arg Phe Ser Pro Asp Phe Thr Phe
225                 230                 235                 240

Gly Phe Glu Glu Ser Leu Glu Val Asp Thr Asn Pro Leu Leu Gly Ala
                245                 250                 255

Gly Lys Phe Ala Thr Asp Pro Ala Val Thr Leu Ala His Glu Leu Ile
            260                 265                 270

His Ala Gly His Arg Leu Tyr Gly Ile Ala Ile Asn Pro Asn Arg Val
        275                 280                 285

Phe Lys Val Asn Thr Asn Ala Tyr Tyr Glu Met Ser Gly Leu Glu Val
290                 295                 300

Ser Phe Glu Glu Leu Arg Thr Phe Gly Gly His Asp Ala Lys Phe Ile
305                 310                 315                 320

Asp Ser Leu Gln Glu Asn Glu Phe Arg Leu Tyr Tyr Tyr Asn Lys Phe
                325                 330                 335

Lys Asp Ile Ala Ser Thr Leu Asn Lys Ala Lys Ser Ile Val Gly Thr
            340                 345                 350

Thr Ala Ser Leu Gln Tyr Met Lys Asn Val Phe Lys Glu Lys Tyr Leu
        355                 360                 365

Leu Ser Glu Asp Thr Ser Gly Lys Phe Ser Val Asp Lys Leu Lys Phe
370                 375                 380

Asp Lys Leu Tyr Lys Met Leu Thr Glu Ile Tyr Thr Glu Asp Asn Phe
385                 390                 395                 400

Val Lys Phe Phe Lys Val Leu Asn Arg Lys Thr Tyr Leu Asn Phe Asp
                405                 410                 415

Lys Ala Val Phe Lys Ile Asn Ile Val Pro Lys Val Asn Tyr Thr Ile
            420                 425                 430

Tyr Asp Gly Phe Asn Leu Arg Asn Thr Asn Leu Ala Ala Asn Phe Asn
        435                 440                 445

Gly Gln Asn Thr Glu Ile Asn Asn Met Asn Phe Thr Lys Leu Lys Asn
450                 455                 460

Phe Thr Gly Leu Phe Glu Phe Tyr Lys Leu Leu Cys Val Arg Gly Ile
465                 470                 475                 480

Ile Thr Ser Lys Thr Lys Ser Leu Asp Lys Gly Tyr Asn Lys Ala Leu
                485                 490                 495

Asn Asp Leu Cys Ile Lys Val Asn Asn Trp Asp Leu Phe Phe Ser Pro
```

```
                500             505             510
Ser Glu Asp Asn Phe Thr Asn Asp Leu Asn Lys Gly Glu Glu Ile Thr
            515             520             525

Ser Asp Thr Asn Ile Glu Ala Ala Glu Glu Asn Ile Ser Leu Asp Leu
            530             535             540

Ile Gln Gln Tyr Tyr Leu Thr Phe Asn Phe Asp Asn Glu Pro Glu Asn
545             550             555             560

Ile Ser Ile Glu Asn Leu Ser Ser Asp Ile Ile Gly Gln Leu Glu Leu
            565             570             575

Met Pro Asn Ile Glu Arg Phe Pro Asn Gly Lys Lys Tyr Glu Leu Asp
            580             585             590

Lys Tyr Thr Met Phe His Tyr Leu Arg Ala Gln Glu Phe Glu His Gly
            595             600             605

Lys Ser Arg Ile Ala Leu Thr Asn Ser Val Asn Glu Ala Leu Leu Asn
            610             615             620

Pro Ser Arg Val Tyr Thr Phe Phe Ser Ser Asp Tyr Val Lys Lys Val
625             630             635             640

Asn Lys Ala Thr Glu Ala Ala Met Phe Leu Gly Trp Val Glu Gln Leu
            645             650             655

Val Tyr Asp Phe Thr Asp Glu Thr Ser Glu Val Ser Thr Thr Asp Lys
            660             665             670

Ile Ala Asp Ile Thr Ile Ile Pro Tyr Ile Gly Pro Ala Leu Asn
            675             680             685

Ile Gly Asn Met Leu Tyr Lys Asp Asp Phe Val Gly Ala Leu Ile Phe
            690             695             700

Ser Gly Ala Val Ile Leu Leu Glu Phe Ile Pro Glu Ile Ala Ile Pro
705             710             715             720

Val Leu Gly Thr Phe Ala Leu Val Ser Tyr Ile Ala Asn Lys Val Leu
            725             730             735

Thr Val Gln Thr Ile Asp Asn Ala Leu Ser Lys Arg Asn Glu Lys Trp
            740             745             750

Asp Glu Val Tyr Lys Tyr Ile Val Thr Asn Trp Leu Ala Lys Val Asn
            755             760             765

Thr Gln Ile Asp Leu Ile Arg Lys Lys Met Lys Glu Ala Leu Glu Asn
            770             775             780

Gln Ala Glu Ala Thr Lys Ala Ile Ile Asn Tyr Gln Tyr Asn Gln Tyr
785             790             795             800

Thr Glu Glu Glu Lys Asn Asn Ile Asn Phe Asn Ile Asp Asp Leu Ser
            805             810             815

Ser Lys Leu Asn Glu Ser Ile Asn Lys Ala Met Ile Asn Ile Asn Lys
            820             825             830

Phe Leu Asn Gln Cys Ser Val Ser Tyr Leu Met Asn Ser Met Ile Pro
            835             840             845

Tyr Gly Val Lys Arg Leu Glu Asp Phe Asp Ala Ser Leu Lys Asp Ala
            850             855             860

Leu Leu Lys Tyr Ile Tyr Asp Asn Arg Gly Thr Leu Ile Gly Gln Val
865             870             875             880

Asp Arg Leu Lys Asp Lys Val Asn Asn Thr Leu Ser Thr Asp Ile Pro
            885             890             895

Phe Gln Leu Ser Lys Tyr Val Asp Asn Gln Arg Leu Leu Ser Thr Phe
            900             905             910

Thr Glu Tyr Ile Lys Asn Ile Ile Asn Thr Ser Ile Leu Asn Leu Arg
            915             920             925
```

-continued

```
Tyr Glu Ser Asn His Leu Ile Asp Leu Ser Arg Tyr Ala Ser Lys Ile
930                 935                 940

Asn Ile Gly Ser Lys Val Asn Phe Asp Pro Ile Asp Lys Asn Gln Ile
945                 950                 955                 960

Gln Leu Phe Asn Leu Glu Ser Ser Lys Ile Glu Val Ile Leu Lys Asn
                965                 970                 975

Ala Ile Val Tyr Asn Ser Met Tyr Glu Asn Phe Ser Thr Ser Phe Trp
                980                 985                 990

Ile Arg Ile Pro Lys Tyr Phe Asn Ser Ile Ser Leu Asn Asn Glu Tyr
                995                 1000                1005

Thr Ile Ile Asn Cys Met Glu Asn Asn Ser Gly Trp Lys Val Ser
    1010                1015                1020

Leu Asn Tyr Gly Glu Ile Ile Trp Thr Leu Gln Asp Thr Gln Glu
    1025                1030                1035

Ile Lys Gln Arg Val Val Phe Lys Tyr Ser Gln Met Ile Asn Ile
    1040                1045                1050

Ser Asp Tyr Ile Asn Arg Trp Ile Phe Val Thr Ile Thr Asn Asn
    1055                1060                1065

Arg Leu Asn Asn Ser Lys Ile Tyr Ile Asn Gly Arg Leu Ile Asp
    1070                1075                1080

Gln Lys Pro Ile Ser Asn Leu Gly Asn Ile His Ala Ser Asn Asn
    1085                1090                1095

Ile Met Phe Lys Leu Asp Gly Cys Arg Asp Thr His Arg Tyr Ile
    1100                1105                1110

Trp Ile Lys Tyr Phe Asn Leu Phe Asp Lys Glu Leu Asn Glu Lys
    1115                1120                1125

Glu Ile Lys Asp Leu Tyr Asp Asn Gln Ser Asn Ser Gly Ile Leu
    1130                1135                1140

Lys Asp Phe Trp Gly Asp Tyr Leu Gln Tyr Asp Lys Pro Tyr Tyr
    1145                1150                1155

Met Leu Asn Leu Tyr Asp Pro Asn Lys Tyr Val Asp Val Asn Asn
    1160                1165                1170

Val Gly Ile Arg Gly Tyr Met Tyr Leu Lys Gly Pro Arg Gly Ser
    1175                1180                1185

Val Met Thr Thr Asn Ile Tyr Leu Asn Ser Ser Leu Tyr Arg Gly
    1190                1195                1200

Thr Lys Phe Ile Ile Lys Lys Tyr Ala Ser Gly Asn Lys Asp Asn
    1205                1210                1215

Ile Val Arg Asn Asn Asp Arg Val Tyr Ile Asn Val Val Val Lys
    1220                1225                1230

Asn Lys Glu Tyr Arg Leu Ala Thr Asn Ala Ser Gln Ala Gly Val
    1235                1240                1245

Glu Lys Ile Leu Ser Ala Leu Glu Ile Pro Asp Val Gly Asn Leu
    1250                1255                1260

Ser Gln Val Val Val Met Lys Ser Lys Asn Asp Gln Gly Ile Thr
    1265                1270                1275

Asn Lys Cys Lys Met Asn Leu Gln Asp Asn Asn Gly Asn Asp Ile
    1280                1285                1290

Gly Phe Ile Gly Phe His Gln Phe Asn Asn Ile Ala Lys Leu Val
    1295                1300                1305

Ala Ser Asn Trp Tyr Asn Arg Gln Ile Glu Arg Ser Ser Arg Thr
    1310                1315                1320
```

```
Leu Gly Cys Ser Trp Glu Phe Ile Pro Val Asp Asp Gly Trp Gly
    1325                1330                1335

Glu Arg Pro Leu
    1340

<210> SEQ ID NO 18
<211> LENGTH: 622
<212> TYPE: PRT
<213> ORGANISM: Artificial Sequence
<220> FEATURE:
<223> OTHER INFORMATION: Synthetic

<400> SEQUENCE: 18

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
    290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335
```

```
Asn Cys Thr Ser Ile Ser Gly Asp Leu His Ile Leu Pro Val Ala Phe
            340                 345                 350

Arg Gly Asp Ser Phe Thr His Thr Pro Pro Leu Asp Pro Gln Glu Leu
        355                 360                 365

Asp Ile Leu Lys Thr Val Lys Glu Ile Thr Gly Phe Leu Leu Ile Gln
    370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
    450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
            500                 505                 510

Asp Lys Cys Asn Leu Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
            580                 585                 590

Cys His Leu Cys His Pro Asn Cys Thr Tyr Gly Cys Thr Gly Pro Gly
        595                 600                 605

Leu Glu Gly Cys Pro Thr Asn Gly Pro Lys Ile Pro Ser Ile
    610                 615                 620

<210> SEQ ID NO 19
<211> LENGTH: 199
<212> TYPE: PRT
<213> ORGANISM: Artificial Sequence
<220> FEATURE:
<223> OTHER INFORMATION: Synthetic

<400> SEQUENCE: 19

Met Lys His Ser Leu Pro Asp Leu Pro Tyr Asp Tyr Gly Ala Leu Glu
1               5                   10                  15

Pro His Ile Asn Ala Gln Ile Met Gln Leu His His Ser Lys His His
            20                  25                  30

Ala Ala Tyr Val Asn Asn Leu Asn Val Thr Glu Glu Lys Tyr Gln Glu
        35                  40                  45

Ala Leu Ala Lys Gly Asp Val Thr Ala Gln Ile Ala Leu Gln Pro Ala
    50                  55                  60

Leu Lys Phe Asn Gly Gly Gly His Ile Asn His Ser Ile Phe Trp Thr
65                  70                  75                  80
```

```
-continued

Asn Leu Ser Pro Asn Gly Gly Gly Glu Pro Lys Gly Glu Leu Leu Glu
                85                  90                  95

Ala Ile Lys Arg Asp Phe Gly Ser Phe Asp Lys Phe Lys Glu Lys Leu
            100                 105                 110

Thr Ala Ala Ser Val Gly Val Gln Gly Ser Gly Trp Gly Trp Leu Gly
            115             120                 125

Phe Asn Lys Glu Arg Gly His Leu Gln Ile Ala Ala Cys Pro Asn Gln
        130             135             140

Asp Pro Leu Gln Gly Thr Thr Gly Leu Ile Pro Leu Leu Gly Ile Asp
145                     150                 155                 160

Val Trp Glu His Ala Tyr Tyr Leu Gln Tyr Lys Asn Val Arg Pro Asp
                165             170                 175

Tyr Leu Lys Ala Ile Trp Asn Val Ile Asn Trp Glu Asn Val Thr Glu
            180             185                 190

Arg Tyr Met Ala Cys Lys Lys
            195
```

TOPICAL COMPOSITIONS AND USES

CROSS-REFERENCE TO RELATED PATENT APPLICATIONS

This application is a U.S. National Stage Application under 35 U.S.C. 371 of International Application No. PCT/CN2018/096448, filed Jul. 20, 2018, which claims priority to PCT/CN2017/093810, filed on Jul. 21, 2017, the contents of all of which are incorporated herein by reference in its entirety in the present disclosure.

BACKGROUND

Botulinum neurotoxins (BoNTs) are naturally occurring neurotoxin produced by bacterium *Clostridium botulinum* and related species. There are seven known serotypes of BoNTs, A, B, C1, D, E, F and G. BoNTs are released from bacteria as a single polypeptide chain and then self-cleaved into a 100 kDa heavy chain and a 50 kDa light chain, which are connected through a single disulfide bond. The heavy chain directs botulinum toxins to presynaptic nerve terminals and mediates internalization of the light chain into the cytoplasm. The light chain of botulinum is a metalloprotease that specifically cleaves SNARE (soluble N-ethylmaleimide-sensitive fusion attachment protein receptor) complex proteins.

SNARE is a large protein superfamily consisting of more than 60 members in mammalian cells. The core SNARE complex is four-α-helical bundle, comprising one helix from each of synaptobrevin (also referred to as vesicle-associated membrane protein, VAMP) and syntaxin-1 and two helices from synaptosomal-associated protein 25 (SNAP-25). The four helices from these SNARE proteins wrap around each other to assemble a coiled-coil quaternary structure. Syntaxin-1 binds to the N-terminal helix of SNAP-25 whereas synaptobrevin helix binds to the C-terminal helix of SNAP-25. The primary role of SNARE complex is to mediate vesicle fusion, for example fusion of synaptic vesicles with presynaptic membrane in neurons.

BoNTs specifically cleave one of the three core SNARE proteins, synaptobrevin, syntaxin-1 or SNAP-25. Inactivation of any of these three proteins will disrupt the formation of core SNARE complex or the interaction of core SNARE complex with other components in the SNARE supercomplex. Blockade of the function of SNARE supercomplex prevents fusion of vesicles with cell membrane and thus prohibits the release of neurotransmitter acetylcholine from axon endings, leading to muscle paralysis.

BoNTs are the most potent naturally occurring toxins in the earth, causing botulism in human with as little as 50 ng substance. In nature, BoNTs mostly infect wild and domesticated animals and are disseminated through invertebrates. According to the origin of toxins, human botulism is categorized into five classes: food-borne botulism, infant botulism, inhalational botulism, iatrogenic botulism (caused by excessive clinical doses of BoNTs) and wound botulism (mostly caused by drug injection). The former two are the most commonly seen human botulism.

The therapeutic use of BoNTs was first proposed during the late 1960s by Alan B. Scott and practiced on children with strabismus in 1977. The extraordinary specificity of BoNTs make them effective agents for human diseases that are characterized by hyperactivity of the nerve terminals. The largest proportion of the therapeutic use of BoNTs is neurological disorders, such as dystonias, sparsticity, hemifacial spasm, hyperhidrosis (excessive sweating) and hypersalivation (excessive saliva). Another important use of BoNTs is to treat urological disorders, such as detrusor sphincter dyssynergia, idiopathic detrusor overactivity, neurogenic detrusor overactivity, urinary retention, anal fissures and benign prostate hyperplasia. Though rarely seen, BoNTs can be used to treat gastroenterological and otolaryngological disorders. BoNTA was approved by United States (US) Food and Drug Administration (FDA) in 2002 for the treatment of moderate-to-severe glabellar rhytids in adult patients of 65 year old or younger. Starting from 2005, BoNTA has become the most widely used noninvasive, physician-assisted cosmetic procedure. While the overall patient satisfaction is above 80%, injectable BoNTA faces many drawbacks such as pain, needle marks, tenderness, bleeding and bruising. In particular, injection of BoNTA in the crow's feet or lateral canthus regions may be associated with high risks of bruising due to thin skin and superficial blood vessels. For some treatments, multiple injections are required to achieve maximum effects.

SUMMARY

The present disclosure provides, in one embodiment, a chimeric polypeptide comprising (a) a botulinum toxin (BoNT) light chain and (b) a first zinc finger motif located to the C-terminal of the BoNT light chain or located to the C-terminal to a BoNT heavy chain which is located C-terminal to the BoNT light chain or bound to the BoNT light chain through a disulfide bond. In some embodiments, the chimeric polypeptide does not include more than 2000 amino acid residues.

In some embodiments, the BoNT light chain and the first zinc finger motif are on the same peptide chain. In some embodiments, the BoNT light chain and the first zinc finger motif are on different peptide chains.

In some embodiments, the chimeric polypeptide further comprises a second zinc finger motif located to the N-terminal of the BoNT light chain. In some embodiments, at least one of the first zinc finger motif and the second zinc finger motif is concatenated to at least a further zinc finger motif. In some embodiments, at least one of the zinc finger motifs is a $Cys_2$-$His_2$ zinc finger motif. In some embodiments, the zinc finger motif contains at least an alanine at residues −1, 2, 3 or 6 of the alpha-helical fragment in the zinc finger motif.

In one example embodiment, a two-chain polypeptide is provided, comprising (a) a first chain comprising a botulinum toxin (BoNT) light chain and three zinc finger motifs located to the N-terminal of the BoNT light chain, and (b) a second chain comprising a BoNT heavy chain three zinc finger motifs located to the C-terminal to a BoNT heavy chain, wherein the BoNT light chain is bound to the BoNT light chain through a disulfide bond. Similarly, in an embodiment, a chimeric polypeptide is provided, comprising, from the N-terminus to the C-terminus, three zinc finger motifs, a botulinum toxin (BoNT) light chain, a BoNT heavy chain, and three more zinc finger motifs.

In some embodiments, at least one of the zinc finger motifs comprises an amino acid sequence selected from the group consisting of SEQ ID NO: 1 and 5 to 7. In some embodiments, the zinc finger motif comprises the amino acid sequence of SEQ ID NO: 1. In some embodiments, the first zinc finger is not longer than 200 amino acid residues away from the C-terminus of the BoNT light chain or the BoNT heavy chain.

In some embodiments, the BoNT is selected from BoNT A, B, C, D, E, F, G or variants having at least 90% sequence identity thereto. In some embodiments, the BoNT is selected from subtypes of BoNT A1-A10, B1-B8, E1-E9, and F1-F7. In some embodiments, the BoNT is BoNT A. In some embodiments, the BoNT light chain comprises the amino acid sequence of SEQ ID NO: 8 or an amino sequence having at least 90% sequence identity to SEQ ID NO: 8. In some embodiments, the BoNT heavy chain comprises the amino acid sequence of SEQ ID NO: 9 or an amino sequence having at least 90% sequence identity to SEQ ID NO: 9.

In some embodiments, the chimeric polypeptide comprises a single-chain polypeptide comprising an amino acid sequence selected from the group consisting of SEQ ID NO: 10 to 17, or a two-chain polypeptide processed from the amino acid sequence.

Also provided, in one embodiment, is a chimeric polypeptide comprising a botulinum toxin (BoNT) light chain and at least a zinc finger motif. In some embodiments, the chimeric polypeptide does not include more than 2000 amino acid residues. In some embodiments, the zinc finger motif is located to the C-terminal to and is no more than 200 amino acid resides away from the BoNT light chain.

Another embodiment of the present disclosure provides a chimeric polypeptide comprising a therapeutic peptide and at least a zinc finger motif located to the C-terminal of the therapeutic peptide, wherein the N-terminus of the zinc finger motif is no more than 100 amino acid residues away from the C-terminus of the therapeutic peptide. In some embodiments, the therapeutic peptide is selected from the group consisting of an epidermal growth factor (EGF) and a superoxide dismutase (SOD).

Uses for manufacture of medicaments and treatment methods are also provided. In some embodiments, a method is provided for administering a BoNT light chain to a mammal subject, comprising topically applying a formulation comprising the chimeric BoNT polypeptide of the present disclosure. The administration, in some embodiments, can alternatively be intramuscular.

In some embodiments, the topical application is on a skin or a mucous membrane of an eye, ear, nose, mouth, lip, urethral opening, anus, or tongue. In some embodiments, the topical application is on a stratum corneum of a skin that has been disrupted. In some embodiments, the disruption is carried out with a needle or microneedle used for delivering the formulation. In some embodiments, the topical application is on a skin of the face or neck of the subject. In some embodiments, the formulation comprises a cream, gel, or spray.

In some embodiments, the subject is in need of treatment of facial wrinkle, dystonias, sparsticity, hemifacial spasm, hyperhidrosis, or hypersalivation.

Polynucleotides encoding the chimeric polypeptides of the present disclosure, cells enclosing the polynucleotides and/or the polypeptides and formulations including the polypeptides are also provided in certain embodiments.

BRIEF DESCRIPTION OF THE DRAWINGS

FIG. 1 illustrates the structures of various BoNTA fusion proteins tested in the examples, including Protein IDs 1-8 which have the sequences of SEQ ID NO:10-17 (Table 4), respectively.

FIG. 2, with panels A and B, shows the results of purification of BoNTA-CPP recombinant fusion protein expressed from *E. coli*. (A) TAT and Pep-1 did not give good yield of protein expression and purification. (B) BoNTA-ZFP (Protein ID: 6) gave good yield of protein expression and purification.

FIG. 3 shows the results of a SNAPtide assay of the in vitro activity of cell-penetrating BoNTA proteins. Positive control is commercially available recombinant BoNTA light chain (BoNTA-LC, R&D Systems). Mock is the SNAPtide alone reaction. Protein IDs 1-8 have the sequences of SEQ ID NO:10-17 (Table 4), respectively

DETAILED DESCRIPTION

Definitions

Figure 4:
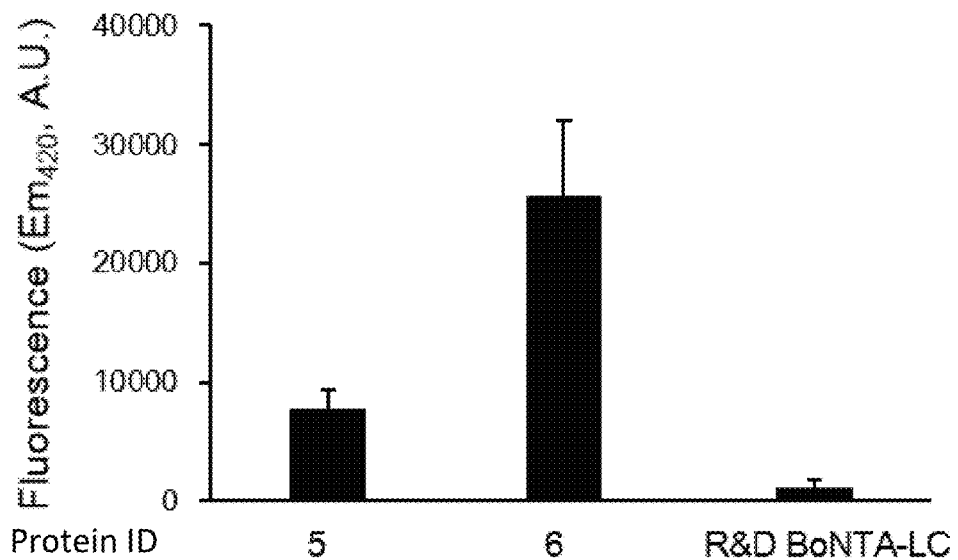
FIG. 4 shows the results of a SNAPtide assay of the cell lysis of human dermal fibroblasts treated with cell-penetrating BoNTA proteins. Negative control is commercially available recombinant BoNTA-LC (R&D Systems). Protein IDs 5-6 have the sequences of SEQ ID NO:14-15 (Table 4), respectively

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present disclosure.

A polynucleotide or polynucleotide region (or a polypeptide or polypeptide region) has a certain percentage (for example, 60%, 65%, 70%, 75%, 80%, 85%, 90%, 95%, 98% or 99%) of "sequence identity" to another sequence means that, when aligned, that percentage of bases (or amino acids) are the same in comparing the two sequences.

The term "an equivalent nucleic acid or polynucleotide" refers to a nucleic acid having a nucleotide sequence having a certain degree of homology, or sequence identity, with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof. Likewise, "an equivalent polypeptide" refers to a polypeptide having a certain degree of homology, or sequence identity, with the amino acid sequence of a reference polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference polypeptide or polynucleotide. In some aspects, the equivalent sequence retains the activity (e.g., epitope-binding) or structure (e.g., salt-bridge) of the reference sequence.

Hybridization reactions can be performed under conditions of different "stringency". In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC. Hybridization reactions can also be performed under "physiological conditions" which is well known to one of skill in the art. A non-limiting example of a physiological condition is the temperature, ionic strength, pH and concentration of $Mg^{2+}$ normally found in a cell.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching. The term "polymorphism" refers to the coexistence of more than one form of a gene or portion thereof. A portion of a gene of which there are at least two different forms, i.e., two different nucleotide sequences, is referred to as a "polymorphic region of a gene". A polymorphic region can be a single nucleotide, the identity of which differs in different alleles.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

As used herein the term "disulfide bond" includes the covalent bond formed between two sulfur atoms. The amino acid cysteine comprises a thiol group that can form a disulfide bond or bridge with a second thiol group.

As used herein, the terms "treat" or "treatment" refer to both therapeutic treatment and prophylactic or preventative measures, wherein the object is to prevent or slow down (lessen) an undesired physiological change or disorder, such as undesired wrinkles. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Chimeric Polypeptide with Zinc Finger Motifs

There is a need on the market for transdermal delivery of BoNT proteins. Transdermal delivery of proteins is inherently difficult, in particular across the skin. Skin is constituted by two layers of cells, known as epidermis and dermis. Epidermis, the topmost layer of skin, is stratified squamous epithelium composing of basal and differentiated keratinocytes. Keratinocytes are the major cell types in epidermis. Keratinocytes in the basal stratum can proliferate through mitosis and undergo multiple cell differentiation stages to become anucleated cells. Anucleated or differentiated keratinocytes are highly organized tissue structure, secreting keratin proteins and lipids, which provide a protective barrier against invading substances such as pathogens.

There has been no success in developing transdermal BoNT compositions. The present disclosure, however, shows that fusion of a BoNT polypeptide to one or more zinc finger motifs (or zinc finger protein domains, or ZFP) can enable the BoNT to penetrate skins. Zinc finger proteins are naturally occurring transcription factors and can be reprogrammed to recognize targeted genomic loci. Zinc finger nucleases-chimeric proteins containing an N-terminal ZFP domain and C-terminal Fok I endonuclease domain-have been shown to be intrinsically cell-permeable. Some of the ZFP include a $Cys_2$-$His_2$ ZFP domain. $Cys_2$-$His_2$ ZFPs consist of approximately 30 amino acids with a $\beta\beta\alpha$ configuration.

This discovery is surprising and unexpected at least for the following reasons. First, the ability to delivering a large protein across animal skin efficiently is itself surprising and unexpected; in particular, it was known that ZFP's cell-penetrating activity is energy-dependent, meaning very limited efficiency, if any at all, would have been expected on stratum corneum, which is the outmost layer of skin that is formed by dead corneocytes which, even if disrupted by physical or chemical means, still constitute an insurmountable barrier to typical biological molecules.

Second, ZFPs are zinc-dependent metalloproteases, and it is also known that the activity of botulinum toxin requires zinc as it can be inhibited by protease inhibitors and zinc chelators. Since both ZFPs and BoNT require the incorporation of zinc ions, it was suspected that the presence of both ZFPs and BoNT in a fusion protein would result in interference between them, leading to decreased activity or even inactivation.

In this context, the instant inventor envisioned that fusing the ZFP at the C-terminal direction of the BoNT could avoid or reduce such interference. In addition or alternatively, the use of a bipartite (tandem) ZFP could ensure that the activity of the ZFP is maintained.

Third, as demonstrated in the experimental examples, the BoNT-ZFP fusion proteins were expressed in high volume from bacterial cells, much higher than when BoNT was fused with TAT or Pep-1, two commonly investigated cell penetration peptides. There was no suggestion to this effect and thus this was unexpected as well.

Figures 2, 3:
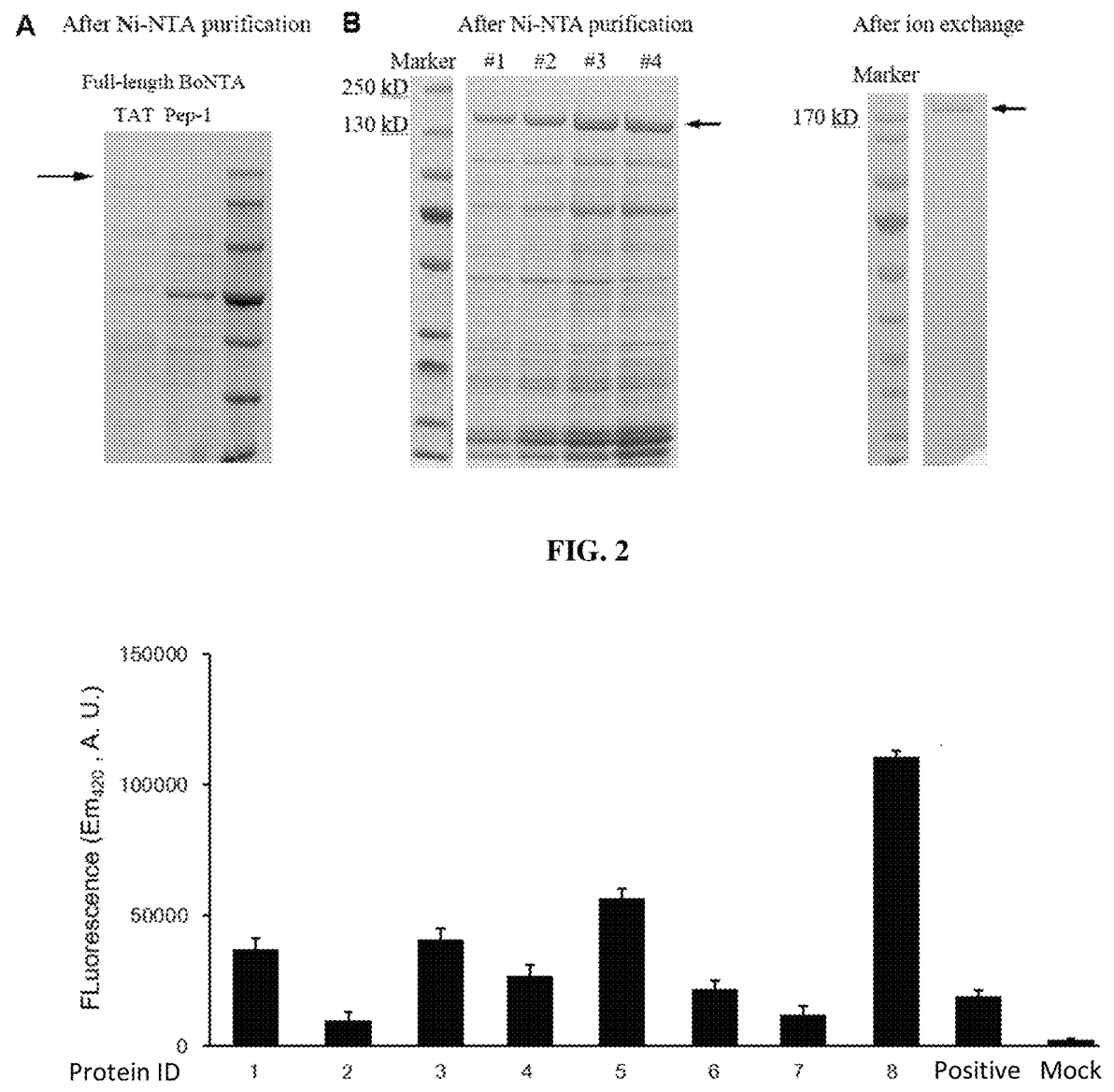

Finally, not only did the expressed BoNT-ZFP fusion proteins exhibit high enzymatic activities (see, e.g., FIG. 3), they also retained such activities after crossing the cell member into the intracellular space (see, e.g., FIG. 4). Still further, when used in an in vivo setting, the topically applied BoNTA-ZFP fusion proteins, preferably on microneedle-treated animal skin, caused muscle paralysis just like the injected BoNTA. This was also surprising as there was no expectation in the art that such therapeutic effects could be achieved with a topical formulation.

In accordance with one embodiment of the present disclosure, therefore, provided is a chimeric (or fusion) polypeptide comprising (a) a botulinum toxin (BoNT) light chain and (b) a zinc finger motif located to the C-terminal of the BoNT light chain.

Also provided, in one embodiment, is a chimeric (or fusion) polypeptide comprising (a) a botulinum toxin (BoNT) light chain (b) a BoNT heavy chain, and (c) a zinc finger motif located to the C-terminal of the BoNT heavy chain. In some embodiments, the light chain and the heavy chain are on the same peptide chain. In some embodiments, the light chain is at the N-terminal side of the heavy chain. In some embodiments, the light chain is at the C-terminal side of the heavy chain. In some embodiments, the light chain and the heavy chain are on different peptide chains and are connected with a disulfide bond.

Also provided, in some embodiments, are chimeric polypeptides comprising a botulinum toxin (BoNT) light chain and at least a zinc finger motif. In one embodiment, the chimeric polypeptides further include a BoNT heavy chain.

The total size of the chimeric polypeptide, in some embodiments, is not greater than 5000 amino acid residues, or alternatively not greater than 4000 amino acid residues, not greater than 3000 amino acid residues, not greater than 2000 amino acid residues, not greater than 1800 amino acid residues, not greater than 1600 amino acid residues, not greater than 1500 amino acid residues, not greater than 1400 amino acid residues, not greater than 1300 amino acid residues, not greater than 1200 amino acid residues, not greater than 1100 amino acid residues, not greater than 1000 amino acid residues, not greater than 900 amino acid residues, not greater than 800 amino acid residues, not greater than 700 amino acid residues, not greater than 600 amino acid residues, not greater than 500 amino acid residues, not greater than 450 amino acid residues, not greater than 400 amino acid residues, not greater than 350 amino acid residues, not greater than 300 amino acid residues, not greater than 250 amino acid residues, or not greater than 200 amino acid residues.

There are at least seven types of botulinum toxin, named type A-G. Type A and B are capable of causing disease in humans, and are also used commercially and medically. Types C-G are less common. Botulinum toxin types A and B are used in medicine to treat various muscle spasms and diseases characterized by overactive muscle. Each BoNT serotype may also have subtypes. For instance, the following subtypes are known: BoNT A1-A10, B1-B8, E1-E9, and F1-F7.

The term BoNT or a particular type or subtype thereof also encompasses their equivalent polynucleotides as well, such as those having certain level (e.g., at least 85%, 90%, 95%, 98%, or 99%) of sequence identity or modified with one or more amino acid residue addition, deletion or substitutions. In some embodiments, the substitutions are conservative amino acid substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE 1A

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

TABLE 1B

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |

TABLE 1B-continued

Conservative Amino Acid Substitutions

| For Amino Acid | Substitution With |
|---|---|
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

In some embodiments, an BoNT peptide includes no more than one, no more than two, or no more than three of the above substitutions from a natural BoNT peptide.

Non-limiting examples of BoNT light chains include SEQ ID NO: 8 (a BoNT A light chain) and amino sequences having at least 90% (or at least 95%, at least 98% or at least 99%) sequence identity to SEQ ID NO: 8. Non-limiting examples of BoNT heavy chains include SEQ ID NO: 9 (a BoNT A heavy chain) and amino sequences having at least 90% (or at least 95%, at least 98% or at least 99%) sequence identity to SEQ ID NO: 9. The amino acid sequences of SEQ ID NO: 8 and 9 are provided in Table 2 below.

TABLE 2

Representative BoNT sequences

| Name | Sequence | SEQ ID NO: |
|---|---|---|
| BoNTA light chain | MPFVNKQFNYKDPVNGVDIAYIKIPNVGQMQPVKAFKIH NKIWVIPERDTFTNPEEGDLNPPPEAKQVPVSYYDSTYL STDNEKDNYLKGVTKLFERIYSTDLGRMLLTSIVRGIPF WGGSTIDTELKVIDTNCINVIQPDGSYRSEELNLVIIGP SADIIQFECKSFGHEVLNLTRNGYGSTQYIRFSPDFTFG FEESLEVDTNPLLGAGKFATDPAVTLAHELIHAGHRLYG IAINPNRVFKVNTNAYYEMSGLEVSFEELRTFGGHDAKF IDSLQENEFRLYYYNKFKDIASTLNKAKSIVGTTASLQY | 8 |

TABLE 2-continued

Representative BoNT sequences

| Name | Sequence | SEQ ID NO: |
|---|---|---|
| BoNTA heavy chain | MKNVFKEKYLLSEDTSGKFSVDKLKFDKLYKMLTEIYTE DNFVKFFKVLNRKTYLNFDKAVFKINIVPKVNYTIYDGF NLRNTNLAANFNGQNTEINNMNFTKLKNFTGLFEF YKLLCVRGIITSKTKSLDKGYNKALNDLCIKVNNWDLFF SPSEDNFTNDLNKGEEITSDTNIEAAEENISLDLIQQYY LTFNFDNEPENISIENLSSDIIGQLELMPNIERFPNGKK YELDKYTMFHYLRAQEFEHGKSRIALTNSVNEALLNPSR VYTFFSSDYVKKVNKATEAAMFLGWVEQLVYDFTDETSE VSTTDKIADITIIIPYIGPALNIGNMLYKDDFVGALIFS GAVILLEFIPEIAIPVLGTFALVSYIANKVLTVQTIDNA LSKRNEKWDEVYKYIVTNWLAKVNTQIDLIRKKMKEALE NQAEATKAIINYQYNQYTEEEKNNINFNIDDLSSKLNES INKAMININKFLNQCSVSYLMNSMIPYGVKRLEDFDASL KDALLKYIYDNRGTLIGQVDRLKDKVNNTLSTDIPFQLS KYVDNQRLLSTFTEYIKNIINTSILNLRYESNHLIDLSR YASKINIGSKVNFDPIDKNQIQLFNLESSKIEVILKNAI VYNSMYENFSTSFWIRIPKYFNSISLNNEYTIINCMENN SGWKVSLNYGEIIWTLQDTQEIKQRVVFKYSQMINISDY INRWIFVTITNNRLNNSKIYINGRLIDQKPISNLGNIHA SNNIMFKLDGCRDTHRYIWIKYFNLFDKELNEKEIKDLY DNQSNSGILKDFWGDYLQYDKPYYMLNLYDPNKYVDVNN VGIRGYMYLKGPRGSVMTTNIYLNSSLYRGTKFIIKKYA SGNKDNIVRNNDRVYINVVVKNKEYRLATNASQAGVEKI LSALEIPDVGNLSQVVVMKSKNDQGITNKCKMNLQDNNG NDIGFIGFHQFNNIAKLVASNWYNRQIERSSRTLGCSWE FIPVDDGWGERPL | 9 |

A "zinc finger motif" is a small protein structural motif that is characterized by the coordination of one or more zinc ions in order to stabilize the fold. In general, zinc fingers coordinate zinc ions with a combination of cysteine and histidine residues. The number and order of these residues can be used to classify different types of zinc fingers (e.g., $Cys_2His_2$, $Cys_4$, and $Cys_6$). Yet another method classifies zinc finger proteins into fold groups based on the overall shape of the protein backbone in the folded domain. The most common fold groups of zinc fingers are the $Cys_2His_2$ (the classic zinc finger), treble clef, zinc ribbon, gag knuckle, $Zn_2/Cys_6$, and TAZ2 domain like.

The $Cys_2His_2$ fold group adopts a simple $\beta\beta\alpha$ fold and has the amino acid sequence motif:

$X_2$-Cys-$X_{2,4}$-Cys-$X_{12}$-His-$X_{3,4,5}$-His.

Individual zinc finger domains can occur as tandem repeats with two, three, or more fingers comprising the DNA-binding domain of the protein.

The zinc finger motifs can be modified to remove or reduce their ability to bind to DNA. For instance, a modified $Cys_2His_2$ contains at least an alanine at residues −1, 2, 3 or 6 of the alpha-helical fragment in the zinc finger motif. Non-limiting examples of zinc finger motifs are shown in Table 3 below. Some of the sequences in Table 3, SEQ ID NO: 1 and 5-7, are individual zinc finger motifs, while a few others (tandem of zinc finger motifs), SEQ ID NO: 2-4, contain multiple concatenated zinc finger motifs. When two or more zinc fingers are used in tandem, they can be located right next to each other or linked via a peptide linker, i.e., a short peptide that is from 1, 2, or 3 amino acid residues to 2, 3, 4, 5, 6, 7, 8, 9 or 10 amino acid residues long). The modified alanine residues of SEQ ID NO: 1 are underlined and bolded.

TABLE 3

Example Zinc finger motifs (ZFP)

| ZFP | Sequence | SEQ ID NO: |
|---|---|---|
| $C_2H_2$ ZFP | EKPYKCPECGKSFS<u>AS</u>AALV<u>A</u>HQRTHTG | 1 |
| $C_2H_2$ $ZFP_2$ | EKPYKCPECGKSFSASAALVAHQRTHTGEKPYKCPE CGKSFSASAALVAHQRTHTG | 2 |
| $C_2H_2$ $ZFP_3$ | EKPYKCPECGKSFSASAALVAHQRTHTGEKPYKCPE CGKSFSASAALVAHQRTHTGEKPYKCPECGKSFSAS AALVAHQRTHTG | 3 |
| $C_2H_2$ $ZFP_4$ | EKPYKCPECGKSFSASAALVAHQRTHTGEKPYKCPE CGKSFSASAALVAHQRTHTGEKPYKCPECGKSFSAS AALVAHQRTHTGEKPYKCPECGKSFSASAALVAHQR THTG | 4 |
| $Zn_2/Cys_6$ ZFP | RIPLSCTICRKRKVKCDKLRPHCQQCTKTGVAHLCH YM | 5 |
| CCHC ZFP | TCYNCGQTGHLSRECPS | 6 |
| $CCHC_5$ ZFP | RRCNCMATRHPLFEVAPNCLNCGKIICEKEGLQPCS YCGQELLSPKDKQEII | 7 |

In some embodiments, the chimeric polypeptide further includes a zinc finger motif located to the N-terminal side of the BoNT light chain. In some embodiments, the chimeric polypeptide further includes a zinc finger motif at the N-terminal side of the BoNT heavy chain. In some embodiments, the chimeric polypeptide is a two-chain polypeptide and includes a zinc finger motif (or a tandem of two zinc fingers or three zinc fingers) at the C-terminal side of the BoNT light chain. In some embodiments, the chimeric polypeptide is a two-chain polypeptide and includes a zinc finger motif (or a tandem of two zinc fingers or three zinc fingers) at the C-terminal side of the BoNT light chain and a zinc finger motif (or a tandem of two zinc fingers or three zinc fingers) at the N-terminal side of the BoNT heavy chain.

In some embodiments, at least one of the zinc finger motifs is concatenated to at least one or two more zinc finger motif to form a bipartite or tripartite zinc finger motif structure (e.g., tandem zinc finger motifs). In some embodiment, the tandem zinc finger motifs have zero, one, two, three, four or five amino acid resides between them.

The distances between the BoNT light chain, heavy and the zinc finger motifs can be adjusted based on preferences and needs. In some embodiments, a zinc finger is not longer than 200 amino acid residues away from the N- or C-terminus of an adjacent BoNT light or heavy chain. In some embodiments, the distance is from 0 to about 150, from 5 to 100, from 10 to 75, from 10 to 50, from 10 to 40, from 10 to 30, from 10 to 20, from 20 to 150, from 20 to 100, from 20 or 50, or from 50 to 100 amino acid resides. In some embodiments, distance is provided by inserting a spacer sequence (e.g., alanine's, glycine's, or the combinations thereof).

Non-limiting examples of chimeric polypeptide sequences are provided in SEQ ID NO: 10 to 17 (Table 3). Some of these sequences include both a BoNT light chain and a BoNT heavy chain and these sequences encompass both the un-cleaved single-chain version and the cleaved two-chain version.

TABLE 4

Representative Chimeric Polypeptide Sequences

| Name | Sequence | SEQ ID NO: |
|---|---|---|
| His-BoNTAFL | MHHHHHHGGSGGSGGSMPFVNKQFNYKDPVNGVDIAYIKIPNVGQMQPVK AFKIHNKIWVIPERDTFTNPEEGDLNPPPEAKQVPVSYYDSTYLSTDNEK DNYLKGVTKLFERIYSTDLGRMLLTSIVRGIPFWGGSTIDTELKVIDTNC INVIQPDGSYRSEELNLVIIGPSADIIQFECKSFGHEVLNLTRNGYGSTQ YIRFSPDFTFGFEESLEVDTNPLLGAGKFATDPAVTLAHELIHAGHRLYG IAINPNRVFKVNTNAYYEMSGLEVSFEELRTFGGHDAKFIDSLQENEFRL YYYNKFKDIASTLNKAKSIVGTTASLQYMKNVFKEKYLLSEDTSGKFSVD KLKFDKLYKMLTEIYTEDNFVKFFKVLNRKTYLNFDKAVFKINIVPKVNY TIYDGFNLRNTNLAANFNGQNTEINNMNFTKLKNFTGLFEFYKLLCVRGI ITSKTKSLDKGYNKALNDLCIKVNNWDLFFSPSEDNFTNDLNKGEEITSD TNIEAAEENISLDLIQQYYLTFNFDNEPENISIENLSSDIIGQLELMPNI ERFPNGKKYELDKYTMFHYLRAQEFEHGKSRIALTNSVNEALLNPSRVYT FFSSDYVKKVNKATEAAMFLGWVEQLVYDFTDETSEVSTTDKIADITIII PYIGPALNIGNMLYKDDFVGALIFSGAVILLEFIPEIAIPVLGTFALVSY IANKVLTVQTIDNALSKRNEKWDEVYKYIVTNWLAKVNTQIDLIRKKMKE ALENQAEATKAIINYQYNQYTEEEKNNINFNIDDLSSKLNESINKAMINI NKFLNQCSVSYLMNSMIPYGVKRLEDFDASLKDALLKYIYDNRGTLIGQV DRLKDKVNNTLSTDIPFQLSKYVDNQRLLSTFTEYIKNIINTSILNLRYE SNHLIDLSRYASKINIGSKVNFDPIDKNQIQLFNLESSKIEVILKNAIVY NSMYENFSTSFWIRIPKYFNSISLNNEYTIINCMENNSGWKVSLNYGEII WTLQDTQEIKQRVVFKYSQMINISDYINRWIFVTITNNRLNNSKIYINGR LIDQKPISNLGNIHASNNIMFKLDGCRDTHRYIWIKYFNLFDKELNEKEI KDLYDNQSNSGILKDFWGDYLQYDKPYYMLNLYDPNKYVDVNNVGIRGYM YLKGPRGSVMTTNIYLNSSLYRGTKFIIKKYASGNKDNIVRNNDRVYINV VVKNKEYRLATNASQAGVEKILSALEIPDVGNLSQVVVMKSKNDQGITNK CKMNLQDNNGNDIGFIGFHQFNNIAKLVASNWYNRQIERSSRTLGCSWEF IPVDDGWGERPL | 10 |
| His-ZFP3-BoNTALC | MHHHHHHGGSGGSGGSEKPYKCPECGKSFSASAALVAHQRTHTGEKPYKC PECGKSFSASAALVAHQRTHTGEKPYKCPECGKSFSASAALVAHQRTHTG GGSGGSGGSMPFVNKQFNYKDPVNGVDIAYIKIPNVGQMQPVKAFKIHNK IWVIPERDTFTNPEEGDLNPPPEAKQVPVSYYDSTYLSTDNEKDNYLKGV TKLFERIYSTDLGRMLLTSIVRGIPFWGGSTIDTELKVIDTNCINVIQPD GSYRSEELNLVIIGPSADIIQFECKSFGHEVLNLTRNGYGSTQYIRFSPD FTFGFEESLEVDTNPLLGAGKFATDPAVTLAHELIHAGHRLYGIAINPNR VFKVNTNAYYEMSGLEVSFEELRTFGGHDAKFIDSLQENEFRLYYYNKFK DIASTLNKAKSIVGTTASLQYMKNVFKEKYLLSEDTSGKFSVDKLKFDKL YKMLTEIYTEDNFVKFFKVLNRKTYLNFDKAVFKINIVPKVNYTIYDGFN LRNTNLAANFNGQNTEINNMNFTKLKNFTGLFEF | 11 |
| His-ZFP3-BoNTAFL | MHHHHHHGGSGGSGGSEKPYKCPECGKSFSASAALVAHQRTHTGEKPYKC PECGKSFSASAALVAHQRTHTGEKPYKCPECGKSFSASAALVAHQRTHTG GGSGGSGGSMPFVNKQFNYKDPVNGVDIAYIKIPNVGQMQPVKAFKIHNK IWVIPERDTFTNPEEGDLNPPPEAKQVPVSYYDSTYLSTDNEKDNYLKGV TKLFERIYSTDLGRMLLTSIVRGIPFWGGSTIDTELKVIDTNCINVIQPD GSYRSEELNLVIIGPSADIIQFECKSFGHEVLNLTRNGYGSTQYIRFSPD FTFGFEESLEVDTNPLLGAGKFATDPAVTLAHELIHAGHRLYGIAINPNR VFKVNTNAYYEMSGLEVSFEELRTFGGHDAKFIDSLQENEFRLYYYNKFK DIASTLNKAKSIVGTTASLQYMKNVFKEKYLLSEDTSGKFSVDKLKFDKL YKMLTEIYTEDNFVKFFKVLNRKTYLNFDKAVFKINIVPKVNYTIYDGFN LRNTNLAANFNGQNTEINNMNFTKLKNFTGLFEFYKLLCVRGIITSKTKS LDKGYNKALNDLCIKVNNWDLFFSPSEDNFTNDLNKGEEITSDTNIEAAE ENISLDLIQQYYLTFNFDNEPENISIENLSSDIIGQLELMPNIERFPNGK KYELDKYTMFHYLRAQEFEHGKSRIALTNSVNEALLNPSRVYTFFSSDYV KKVNKATEAAMFLGWVEQLVYDFTDETSEVSTTDKIADITIIIPYIGPAL NIGNMLYKDDFVGALIFSGAVILLEFIPEIAIPVLGTFALVSYIANKVLT VQTIDNALSKRNEKWDEVYKYIVTNWLAKVNTQIDLIRKKMKEALENQAE ATKAIINYQYNQYTEEEKNNINFNIDDLSSKLNESINKAMININKFLNQC SVSYLMNSMIPYGVKRLEDFDASLKDALLKYIYDNRGTLIGQVDRLKDKV NNTLSTDIPFQLSKYVDNQRLLSTFTEYIKNIINTSILNLRYESNHLIDL SRYASKINIGSKVNFDPIDKNQIQLFNLESSKIEVILKNAIVYNSMYENF STSFWIRIPKYFNSISLNNEYTIINCMENNSGWKVSLNYGEIIWTLQDTQ EIKQRVVFKYSQMINISDYINRWIFVTITNNRLNNSKIYINGRLIDQKPI SNLGNIHASNNIMFKLDGCRDTHRYIWIKYFNLFDKELNEKEIKDLYDNQ SNSGILKDFWGDYLQYDKPYYMLNLYDPNKYVDVNNVGIRGYMYLKGPRG SVMTTNIYLNSSLYRGTKFIIKKYASGNKDNIVRNNDRVYINVVVKNKEY RLATNASQAGVEKILSALEIPDVGNLSQVVVMKSKNDQGITNKCKMNLQD NNGNDIGFIGFHQFNNIAKLVASNWYNRQIERSSRTLGCSWEFIPVDDGW GERPL | 12 |
| BoNTALC-ZFP3-His | MPFVNKQFNYKDPVNGVDIAYIKIPNVGQMQPVKAFKIHNKIWVIPERDT FTNPEEGDLNPPPEAKQVPVSYYDSTYLSTDNEKDNYLKGVTKLFERIYS TDLGRMLLTSIVRGIPFWGGSTIDTELKVIDTNCINVIQPDGSYRSEELN LVIIGPSADIIQFECKSFGHEVLNLTRNGYGSTQYIRFSPDFTFGFEESL EVDTNPLLGAGKFATDPAVTLAHELIHAGHRLYGIAINPNRVFKVNTNAY YEMSGLEVSFEELRTFGGHDAKFIDSLQENEFRLYYYNKFKDIASTLNKA | 13 |

TABLE 4-continued

| Representative Chimeric Polypeptide Sequences | | |
|---|---|---|
| Name | Sequence | SEQ ID NO: |
| | KSIVGTTASLQYMKNVFKEKYLLSEDTSGKFSVDKLKFDKLYKMLTEIYT<br>EDNFVKFFKVLNRKTYLNFDKAVFKINIVPKVNYTIYDGFNLRNTNLAAN<br>FNGQNTEINNMNFTKLKNFTGLFEFGGSGGSGGSEKPYKCPECGKSFSAS<br>AALVAHQRTHTGEKPYKCPECGKSFSASAALVAHQRTHTGEKPYKCPECG<br>KSFSASAALVAHQRTHTGGGSGGSGGSHHHHHH | |
| BoNTAFL-<br>ZFP3-His | MPFVNKQFNYKDPVNGVDIAYIKIPNVGQMQPVKAFKIHNKIWVIPERDT<br>FTNPEEGDLNPPPEAKQVPVSYYDSTYLSTDNEKDNYLKGVTKLFERIYS<br>TDLGRMLLTSIVRGIPFWGGSTIDTELKVIDTNCINVIQPDGSYRSEELN<br>LVIIGPSADIIQFECKSFGHEVLNLTRNGYGSTQYIRFSPDFTFGFEESL<br>EVDTNPLLGAGKFATDPAVTLAHELIHAGHRLYGIAINPNRVFKVNTNAY<br>YEMSGLEVSFEELRTFGGHDAKFIDSLQENEFRLYYYNKFKDIASTLNKA<br>KSIVGTTASLQYMKNVFKEKYLLSEDTSGKFSVDKLKFDKLYKMLTEIYT<br>EDNFVKFFKVLNRKTYLNFDKAVFKINIVPKVNYTIYDGFNLRNTNLAAN<br>FNGQNTEINNMNFTKLKNFTGLFEFYKLLCVRGIITSKTKSLDKGYNKAL<br>NDLCIKVNNWDLFFSPSEDNFTNDLNKGEEITSDTNIEAAEENISLDLIQ<br>QYYLTFNFDNEPENISIENLSSDIIGQLELMPNIERFPNGKKYELDKYTM<br>FHYLRAQEFEHGKSRIALTNSVNEALLNPSRVYTFFSSDYVKKVNKATEA<br>AMFLGWVEQLVYDFTDETSEVSTTDKIADITIIIPYIGPALNIGNMLYKD<br>DFVGALIFSGAVILLEFIPEIAIPVLGTFALVSYIANKVLTVQTIDNALS<br>KRNEKWDEVYKYIVTNWLAKVNTQIDLIRKKMKEALENQAEATKAIINYQ<br>YNQYTEEEKNNINFNIDDLSSKLNESINKAMININKFLNQCSVSYLMNSM<br>IPYGVKRLEDFDASLKDALLKYIYDNRGTLIGQVDRLKDKVNNTLSTDIP<br>FQLSKYVDNQRLLSTFTEYIKNIINTSILNLRYESNHLIDLSRYASKINI<br>GSKVNFDPIDKNQIQLFNLESSKIEVILKNAIVYNSMYENFSTSFWIRIP<br>KYFNSISLNNEYTIINCMENNSGWKVSLNYGEIIWTLQDTQEIKQRVVFK<br>YSQMINISDYINRWIFVTITNNRLNNSKIYINGRLIDQKPISNLGNIHAS<br>NNIMFKLDGCRDTHRYIWIKYFNLFDKELNEKEIKDLYDNQSNSGILKDF<br>WGDYLQYDKPYYMLNLYDPNKYVDVNNVGIRGYMYLKGPRGSVMTTNIYL<br>NSSLYRGTKFIIKKYASGNKDNIVRNNDRVYINVVVKNKEYRLATNASQA<br>GVEKILSALEIPDVGNLSQVVVMKSKNDQGITNKCKMNLQDNNGNDIGFI<br>GFHQFNNIAKLVASNWYNRQIERSSRTLGCSWEFIPVDDGWGERPLGGSG<br>GSGGSEKPYKCPECGKSFSASAALVAHQRTHTGEKPYKCPECGKSFSASA<br>ALVAHQRTHTGEKPYKCPECGKSFSASAALVAHQRTHTGGGSGGSGGSHH<br>HHHH | 14 |
| His-ZFP3-<br>BoNTAFL-<br>ZFP3 | MHHHHHHGGSGGSGGSEKPYKCPECGKSFSAsAALvAHQRTHTGEKPYKC<br>PECGKSFSASAALVAHQRTHTGEKPYKCPECGKSFSASAALVAHQRTHTG<br>GGSGGSGGSMPFVNKQFNYKDPVNGVDIAYIKIPNVGQMQPVKAFKIHNK<br>IWVIPERDTFTNPEEGDLNPPPEAKQVPVSYYDSTYLSTDNEKDNYLKGV<br>TKLFERIYSTDLGRMLLTSIVRGIPFWGGSTIDTELKVIDTNCINVIQPD<br>GSYRSEELNLVIIGPSADIIQFECKSFGHEVLNLTRNGYGSTQYIRFSPD<br>FTFGFEESLEVDTNPLLGAGKFATDPAVTLAHELIHAGHRLYGIAINPNR<br>VFKVNTNAYYEMSGLEVSFEELRTFGGHDAKFIDSLQENEFRLYYYNKFK<br>DIASTLNKAKSIVGITASLQYMKNVFKEKYLLSEDTSGKFSVDKLKFDKL<br>YKMLTEIYTEDNFVKFFKVLNRKTYLNFDKAVFKINIVPKVNYTIYDGFN<br>LRNTNLAANFNGQNTEINNMNFTKLKNFTGLFEFYKLLCVRGIITSKTKS<br>LDKGYNKALNDLCIKVNNWDLFFSPSEDNFTNDLNKGEEITSDTNIEAAE<br>ENISLDLIQQYYLTFNFDNEPENISIENLSSDIIGQLELMPNIERFPNGK<br>KYELDKYTMFHYLRAQEFEHGKSRIALTNSVNEALLNPSRVYTFFSSDYV<br>KKVNKATEAAMFLGWVEQLVYDFTDETSEVSTTDKIADITIIIPYIGPAL<br>NIGNMLYKDDFVGALIFSGAVILLEFIPEIAIPVLGTFALVSYIANKVLT<br>VQTIDNALSKRNEKWDEVYKYIVTNWLAKVNTQIDLIRKKMKEALENQAE<br>ATKAIINYQYNQYTEEEKNNINFNIDDLSSKLNESINKAMININKFLNQC<br>SVSYLMNSMIPYGVKRLEDFDASLKDALLKYIYDNRGTLIGQVDRLKDKV<br>NNTLSTDIPFQLSKYVDNQRLLSTFTEYIKNIINTSILNLRYESNHLIDL<br>SRYASKINIGSKVNFDPIDKNQIQLFNLESSKIEVILKNAIVYNSMYENF<br>STSFWIRIPKYFNSISLNNEYTIINCMENNSGWKVSLNYGEIIWTLQDTQ<br>EIKQRVVFKYSQMINISDYINRWIFVTITNNRLNNSKIYINGRLIDQKPI<br>SNLGNIHASNNIMFKLDGCRDTHRYIWIKYFNLFDKELNEKEIKDLYDNQ<br>SNSGILKDFWGDYLQYDKPYYMLNLYDPNKYVDVNNVGIRGYMYLKGPRG<br>SVMTTNIYLNSSLYRGTKFIIKKYASGNKDNIVRNNDRVYINVVVKNKEY<br>RLATNASQAGVEKILSALEIPDVGNLSQVVVMKSKNDQGITNKCKMNLQD<br>NNGNDIGFIGFHQFNNIAKLVASNWYNRQIERSSRTLGCSWEFIPVDDGW<br>GERPLGGSGGSGGSEKPYKCPECGKSFSASAALVAHQRTHTGEKPYKCPE<br>CGKSFSASAALVAHQRTHTGEKPYKCPECGKSFSASAALVAHQRTHTG | 15 |
| His-TAT-<br>BoNTAFL | MHHHHHHGGSGGSGGSGRKKRRQRRRPQGGSGGSGGSMPFVNKQFNYKDP<br>VNGVDIAYIKIPNVGQMQPVKAFKIHNKIWVIPERDTFTNPEEGDLNPPP<br>EAKQVPVSYYDSTYLSTDNEKDNYLKGVTKLFERIYSTDLGRMLLTSIVR<br>GIPFWGGSTIDTELKVIDTNCINVIQPDGSYRSEELNLVIIGPSADIIQF<br>ECKSFGHEVLNLTRNGYGSTQYIRFSPDFTFGFEESLEVDTNPLLGAGKF<br>ATDPAVTLAHELIHAGHRLYGIAINPNRVFKVNTNAYYEMSGLEVSFEEL<br>RTFGGHDAKFIDSLQENEFRLYYYNKFKDIASTLNKAKSIVGTTASLQYM<br>KNVFKEKYLLSEDTSGKFSVDKLKFDKLYKMLTEIYTEDNFVKFFKVLNR<br>KTYLNFDKAVFKINIVPKVNYTIYDGFNLRNTNLAANFNGQNTEINNMNF | 16 |

TABLE 4-continued

Representative Chimeric Polypeptide Sequences

| Name | Sequence | SEQ ID NO: |
|---|---|---|
| | TKLKNFTGLFEFYKLLCVRGIITSKTKSLDKGYNKALNDLCIKVNNWDLF<br>FSPSEDNFTNDLNKGEEITSDTNIEAAEENISLDLIQQYYLTFNFDNEPE<br>NISIENLSSDIIGQLELMPNIERFPNGKKYELDKYTMFHYLRAQEFEHGK<br>SRIALTNSVNEALLNPSRVYTFFSSDYVKKVNKATEAAMFLGWVEQLVYD<br>FTDETSEVSTTDKIADITIIIPYIGPALNIGNMLYKDDFVGALIFSGAVI<br>LLEFIPEIAIPVLGTFALVSYIANKVLTVQTIDNALSKRNEKWDEVYKYI<br>VTNWLAKVNTQIDLIRKKMKEALENQAEATKAIINYQYNQYTEEEKNNIN<br>FNIDDLSSKLNESINKAMININKFLNQCSVSYLMNSMIPYGVKRLEDFDA<br>SLKDALLKYIYDNRGTLIGQVDRLKDKVNNTLSTDIPFQLSKYVDNQRLL<br>STFTEYIKNIINTSILNLRYESNHLIDLSRYASKINIGSKVNFDPIDKNQ<br>IQLFNLESSKIEVILKNAIVYNSMYENFSTSFWIRIPKYFNSISLNNEYT<br>IINCMENNSGWKVSLNYGEIIWTLQDTQEIKQRVVFKYSQMINISDYINR<br>WIFVTITNNRLNNSKIYINGRLIDQKPISNLGNIHASNNIMFKLDGCRDT<br>HRYIWIKYFNLFDKELNEKEIKDLYDNQSNSGILKDFWGDYLQYDKPYYM<br>LNLYDPNKYVDVNNVGIRGYMYLKGPRGSVMTTNIYLNSSLYRGTKFIIK<br>KYASGNKDNIVRNNDRVYINVVVKNKEYRLATNASQAGVEKILSALEIPD<br>VGNLSQVVVMKSKNDQGITNKCKMNLQDNNGNDIGFIGFHQFNNIAKLVA<br>SNWYNRQIERSSRTLGCSWEFIPVDDGWGERPL | |
| His-Pep1-<br>BoNTAFL | MHHHHHHGGSGGSGGSKETWWETWWTEWSQPKKKRKVGGSGGSGGSMPFV<br>NKQFNYKDPVNGVDIAYIKIPNVGQMQPVKAFKIHNKIWVIPERDTFTNP<br>EEGDLNPPPEAKQVPVSYYDSTYLSTDNEKDNYLKGVTKLFERIYSTDLG<br>RMLLTSIVRGIPFWGGSTIDTELKVIDTNCINVIQPDGSYRSEELNLVII<br>GPSADIIQFECKSFGHEVLNLTRNGYGSTQYIRFSPDFTFGFEESLEVDT<br>NPLLGAGKFATDPAVTLAHELIHAGHRLYGIAINPNRVFKVNTNAYYEMS<br>GLEVSFEELRTFGGHDAKFIDSLQENEFRLYYYNKFKDIASTLNKAKSIV<br>GTTASLQYMKNVFKEKYLLSEDTSGKFSVDKLKFDKLYKMLTEIYTEDNF<br>VKFFKVLNRKTYLNFDKAVFKINIVPKVNYTIYDGFNLRNTNLAANFNGQ<br>NTEINNMNFTKLKNFTGLFEFYKLLCVRGIITSKTKSLDKGYNKALNDLC<br>IKVNNWDLFFSPSEDNFTNDLNKGEEITSDTNIEAAEENISLDLIQQYYL<br>TFNFDNEPENISIENLSSDIIGQLELMPNIERFPNGKKYELDKYTMFHYL<br>RAQEFEHGKSRIALTNSVNEALLNPSRVYTFFSSDYVKKVNKATEAAMFL<br>GWVEQLVYDFIDETSEVSTTDKIADITIIIPYIGPALNIGNMLYKDDFVG<br>ALIFSGAVILLEFIPEIAIPVLGTFALVSYIANKVLTVQTIDNALSKRNE<br>KWDEVYKYIVINWLAKVNTQIDLIRKKMKEALENQAEATKAIINYQYNQY<br>TEEEKNNINFNIDDLSSKLNESINKAMININKFLNQCSVSYLMNSMIPYG<br>VKRLEDFDASLKDALLKYIYDNRGTLIGQVDRLKDKVNNTLSTDIPFQLS<br>KYVDNQRLLSTFTEYIKNIINTSILNLRYESNHLIDLSRYASKINIGSKV<br>NFDPIDKNQIQLFNLESSKIEVILKNAIVYNSMYENFSTSFWIRIPKYFN<br>SISLNNEYTIINCMENNSGWKVSLNYGEIIWTLQDTQEIKQRVVFKYSQM<br>INISDYINRWIFVTITNNRLNNSKIYINGRLIDQKPISNLGNIHASNNIM<br>FKLDGCRDTHRYIWIKYFNLFDKELNEKEIKDLYDNQSNSGILKDFWGDY<br>LQYDKPYYMLNLYDPNKYVDVNNVGIRGYMYLKGPRGSVMTTNIYLNSSL<br>YRGTKFIIKKYASGNKDNIVRNNDRVYINVVVKNKEYRLATNASQAGVEK<br>ILSALEIPDVGNLSQVVVMKSKNDQGITNKCKMNLQDNNGNDIGFIGFHQ<br>FNNIAKLVASNWYNRQIERSSRTLGCSWEFIPVDDGWGERPL | 17 |

It is further contemplated that the present technology is also applicable to other therapeutic peptide such as epidermal growth factor (EGF) and superoxide dismutase (SOD), without limitation. Accordingly, in one embodiment, the present disclosure provides a chimeric polypeptide comprising a therapeutic peptide and at least a zinc finger motif. In some embodiments, the zinc finger motif is located to the C-terminal side of the therapeutic peptide. In some embodiments, the zinc finger motif is no more than 100 amino acid residues (or no more than 90, 80, 70, 60, 50, 40, 30, 20, 10 or 5 amino acid residues) away from the therapeutic peptide. In some embodiments, the zinc finger motif is concatenated to another zinc finger motif to form a bipartite zinc finger motif. In some embodiments, the chimeric polypeptide includes a zinc finger motif (or bipartite one) at both the N-terminal side and the C-terminal side of the therapeutic peptide.

In some embodiments, the therapeutic peptide is selected from EGF and SOD, example sequences of which are shown in Table 5. Examples of zinc finger motifs, examples spacer sequences and distances between zinc finger motifs and the therapeutic peptides are also described herein.

TABLE 5

Representative Therapeutic Peptide Sequences

| Name | Sequence | SEQ ID NO: |
|---|---|---|
| EGF | LEEKKVCQGTSNKLTQLGTFEDHFLSLQRMFNNCEVVLG<br>NLEITYVQRNYDLSFLKTIQEVAGYVLIALNTVERIPLE<br>NLQIIRGNMYYENSYALAVLSNYDANKTGLKELPMRNLQ<br>EILHGAVRFSNNPALCNVESIQWRDIVSSDFLSNMSMDF<br>QNHLGSCQKCDPSCPNGSCWGAGEENCQKLTKIICAQQC<br>SGRCRGKSPSDCCHNQCAAGCTGPRESDCLVCRKFRDEA<br>TCKDTCPPLMLYNPTTYQMDVNPEGKYSFGATCVKKCPR<br>NYVVTDHGSCVRACGADSYEMEEDGVRKCKKCEGPCRKV<br>CNGIGIGEFKDSLSINATNIKHFKNCTSISGDLHILPVA<br>FRGDSFTHTPPLDPQELDILKTVKEITGFLLIQAWPENR<br>TDLHAFENLEIIRGRTKQHGQFSLAVVSLNITSLGLRSL<br>KEISDGDVIISGNKNLCYANTINWKKLFGTSGQKTKIIS<br>NRGENSCKATGQVCHALCSPEGCWGPEPRDCVSCRNVSR<br>GRECVDKCNLLEGEPREFVENSECIQCHPECLPQAMNIT<br>CTGRGPDNCIQCAHYIDGPHCVKTCPAGVMGENNTLVWK<br>YADAGHVCHLCHPNCTYGCTGPGLEGCPTNGPKIPSI | 18 |

TABLE 5-continued Representative Therapeutic Peptide Sequences

| Name | Sequence | SEQ ID NO: |
|---|---|---|
| SOD | MKHSLPDLPYDYGALEPHINAQIMQLHHSKHHAAYVNNL NVTEEKYQEALAKGDVTAQIALQPALKFNGGGHINHSIF WTNLSPNGGGEPKGELLEAIKRDFGSFDKFKEKLTAASV GVQGSGWGWLGFNKERGHLQIAACPNQDPLQGTTGLIPL LGIDVWEHAYYLQYKNVRPDYLKAIWNVINWENVTERYM ACKK | 19 |

In some embodiments, the polypeptides may be conjugated to therapeutic agents, prodrugs, peptides, proteins, enzymes, viruses, lipids, biological response modifiers, pharmaceutical agents, or PEG. The polypeptides may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

The polypeptides can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

The polypeptides can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The present disclosure also provides isolated polynucleotides or nucleic acid molecules encoding the polypeptides, variants or derivatives thereof of the disclosure. The polynucleotides of the present disclosure may encode the entire heavy and light chain of the polypeptides, variants or derivatives thereof on the same polynucleotide molecule or on separate polynucleotide molecules. Additionally, the polynucleotides of the present disclosure may encode portions of the heavy and light chain of the polypeptides, variants or derivatives thereof on the same polynucleotide molecule or on separate polynucleotide molecules.

Polynucleotides encoding a fusion polypeptide or domains thereof can be inserted into an "expression vector." The term "expression vector" refers to a genetic construct such as a plasmid, virus or other vehicle known in the art that can be engineered to contain a polynucleotide encoding a polypeptide of the disclosure. Such expression vectors are typically plasmids that contain a promoter sequence that facilitates transcription of the inserted genetic sequence in a host cell. The expression vector typically contains an origin of replication, and a promoter, as well as genes that allow phenotypic selection of the transformed cells (e.g., an antibiotic resistance gene). Various promoters, including inducible and constitutive promoters, can be utilized in the disclosure. Typically, the expression vector contains a replicon site and control sequences that are derived from a species compatible with the host cell.

Transformation or transfection of a host cell with a polynucleotide can be carried out using conventional techniques well known to those skilled in the art. For example, where the host cell is *E. coli*, competent cells that are capable of DNA uptake can be prepared using the $CaCl_2$, $MgCl_2$ or RbCl methods known in the art. Alternatively, physical means, such as electroporation or microinjection can be used. Electroporation allows transfer of a polynucleotide into a cell by high voltage electric impulse. Additionally, polynucleotides can be introduced into host cells by protoplast fusion, using methods well known in the art. Suitable methods for transforming eukaryotic cells, such as electroporation and lipofection, also are known.

"Host cells" encompassed by of the disclosure are any cells in which the polynucleotides of the disclosure can be used to express the fusion polypeptide or functional domains thereof. The term also includes any progeny of a host cell. Host cells, which are useful, include bacterial cells (e.g., *Clostridium botulinum*), fungal cells (e.g., yeast cells), insect cells (e.g., *Spodoptera*), plant cells and animal cells. A fusion polypeptide of the disclosure can be produced by expression of polynucleotide encoding a fusion polypeptide in prokaryotes. These include, but are not limited to, microorganisms, such as bacteria transformed with recombinant bacteriophage DNA, plasmid DNA, or cosmid DNA expression vectors encoding a fusion polypeptide of the disclosure. Introduction of the construct into the host cell can be effected by calcium phosphate transfection, DEAE-Dextran mediated transfection, or electroporation.

The constructs can be expressed in *Clostridium botulinum*, which is where BoNT proteins are naturally produced. It is a surprising discovery of the present disclosure that the chimeric proteins containing a BoNT light chain and/or heavy chain can be efficiently produced in insect cells (e.g., *Spodoptera frugiperda* Sf9). Accordingly, in one embodiment, the host cell can be an insect cell, such as a Lepidoptera cell, a Noctuidae cell, a *Spodoptera* cell, and a *Spodoptera frugiperda* cell.

For long-term, high-yield production of recombinant proteins, stable expression is typically used. Rather than using expression vectors that contain viral origins of replication, host cells can be transformed with the cDNA encoding a fusion polypeptide of the disclosure controlled by appropriate expression control elements (e.g., promoter, enhancer, sequences, transcription terminators, polyadenylation sites, and the like), and a selectable marker. The selectable marker confers resistance to a selective killing agent and upon stable integration of the heterologous polynucleotide, allows growth of resistant cells. Such resistant cells grow to form foci that, in turn, can be cloned and expanded into cell lines.

Treatment Methods and Uses

As described herein, the zinc finger motif-containing chimeric (fusion) polypeptides of the present disclosure can be effectively delivered transdermally. Therefore, depending on the fused therapeutic protein, the chimeric polypeptides have therapeutic uses.

Chimeric polypeptides that include a BoNT light chain, optionally further with a BoNT heavy chain, have broad cosmetic and therapeutic applications. For cosmetic applications, such chimeric polypeptides can be useful for treating wrinkles, adjusting the corners of the mouth or lines from the upper lips. In therapeutics, the chimeric polypeptides can be useful for treating neurological disorders such as dystonias, sparsticity, hemifacial spasm, hyperhidrosis (excessive sweating), hypersalivation (excessive saliva). The chimeric polypeptides may also be used for urological disorders such as detrusor sphincter dyssynergia, idiopathic detrusor overactivity, neurogenic detrusor overactivity, urinary retention, anal fissures, benign prostate hyperplasia.

Still further indications gastroenterological, otolaryngological disorders or other medical conditions. In some embodiments, the chimeric polypeptides are used for treating facial wrinkle, dystonias, sparsticity, hemifacial spasm, hyperhidrosis, or hypersalivation.

Chimeric polypeptides that include an EGF, in another example, can be used to treat conditions such as diabetic foot ulcers, or in general wound healing. Still in another example, a chimeric polypeptide that includes a SOD peptide can be used to reduce free radical damage to skin, e.g., to reduce fibrosis following radiation for breast cancer.

The topical application of the chimeric polypeptides can be carried out on a dermal position of a subject, such as on a skin or at a mucous membrane of an eye, ear, nose, mouth, lip, urethral opening, anus, or tongue. Specific examples of locations include, without limitation, face, neck, head, legs, shoulders, back, palms, feet, groin, axilla, elbow, arms, knee, buttocks, torso, and pelvis. Likewise, the chimeric polypeptides can also be administered intramuscularly at this locations.

In some embodiment, therefore, a method is provided administering a therapeutic peptide (e.g., BoNT, EGF or SOD) to a mammal subject, comprising topically or intramuscularly applying a formulation containing a chimeric polypeptide that includes a zinc finger motif and the therapeutic peptide to the mammal subject.

When the topically application is on a stratum corneum of a skin, in some embodiments, the stratum corneum is preferably disrupted. Disruption of the stratum corneum may be carried out with a needle, such as a microneedle as illustrated in the experimental examples. Alternatively, the application can be intramuscular.

A specific dosage and treatment regimen for any particular patient will depend upon a variety of factors, including the particular polypeptides, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Compositions

The present disclosure also provides pharmaceutical compositions. Such compositions comprise an effective amount of a chimeric polypeptide, and an acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of gels, creams, sprays, solutions, suspensions, emulsion, tablets, pills, capsules, powders, sustained-release formulations and the like. The composition can be formulated as a suppository, with traditional binders and carriers such as triglycerides.

Kits and packages are also provided in certain embodiments that includes a chimeric polypeptide, or a composition or formulation thereof, and instructions for using the chimeric polypeptide, composition or formulation. In some embodiments, the kit or package further includes a needle or microneedle for delivering the chimeric polypeptide, composition or formulation. As noted above, the microneedle can be useful for disrupting the stratum corneum of a skin thereby improving delivery.

Animal Test Methods

Presently, the rat Digit Abduction Score (DAS) assay is the primary physiological model for assessing BoNT-induced skeletal muscle paralysis. This assay is not fully objective and is prone to errors. In some embodiments, the present disclosure describes new methods for quantitatively measuring BoNT-induced skeletal muscle paralysis in animals.

In one example, the animal, before or after receiving a testing agent, is placed on a treadmill. When the treadmill is started, the animal is forced to move as long as the animal is physically capable with a maximum running time of 30 min. The duration of the movement, distance or time, can quantitatively reflect the effect of the testing agent (with suitable controls such as animal without being give the testing agent).

In another example, the animal is placed on a balance beam on which the animal is instructed to walk to the other end. Muscle paralysis resulting in reduced capability to keep balance will be reflected by the time it takes for the animal to traverse the balance beam.

In yet another example, the footprint of the animal is measured, while standing or walking (e.g., on a treadmill). Sizes of the footprints can also be quantitative measurement of the degree of paralysis.

EXAMPLES

Example 1. Expression and Purification of BoNTA-CPP Fusion Proteins from *Escherichia coli*

This experiment demonstrates that BoNTA-CPP (cell penetration peptide) fusion proteins can be expressed and purified from *E. coli* cells.

Methods

Protein Expression pET28b vectors containing different BoNTA constructs (Protein ID: 1~8; FIG. 1) were transformed into BL21(DE3) *E. coli* cells. The sequences of these constructs are provided in SEQ ID NO: 10-17. $His_6$: histidine tag; BoNTA-LC:

BoNT A light chain; BoNTA-HC: BoNT A heavy chain; ZFP$_2$: tandem zinc finger peptides (SEQ ID NO: 1); TAT: transactivator of transcription peptide; Pep-1: pep-1 peptide. TAT and Pep-1 are known cell penetration peptides (CPP).

A single colony was picked from the agar plate and grown in 10 mL lysogeny broth (LB) medium supplemented with 50 µg/mL kanamycin and 90 µM ZnCl$_2$ at 37° C. overnight. The next day, 10 mL of the starter culture was inoculated into 1 liter LB medium supplemented with 50 g/mL kanamycin and 90 µM ZnCl$_2$ and grown to an OD$_{600}$ of 0.8. Protein expression was induced with 0.1 mM isopropyl-β-D-thiogalactopyranoside (IPTG) at 25° C. for 4 h. Cell pellet was harvested by centrifugation at 5,000 rpm for 10 min.

Protein Purification

Cell pellet from 2 liter culture (approximately 30 gram) was resuspended in 200 mL BoNTA lysis buffer (20 mM HEPES, pH 7.0, 500 mM NaCl, 0.01% Triton X-100, lx protease cocktail (Roche) and 10% glycerol) and sonicated on ice for three times. Lysed cells were centrifuged at 25,000 g for 1 h at 4° C. and the supernatant was transferred to a new tube. To this supernatant was added 1 mL (settled volume) equilibrated Ni-NTA resins (Qiagen). BoNTA proteins containing His$_6$ tag was allowed to bind with the resins for 30 min with rotation. The resins were transferred to a column and the flow-through was discarded. The resins were washed with 50 mL BoNTA wash buffer (20 mM HEPES, pH 7.0, 500 mM NaCl and 10% glycerol, 20 mM imidazole) and then eluted with 50 mL BoNTA elution buffer (20 mM HEPES, pH 7.0, 500 mM NaCl and 10% glycerol, 300 mM imidazole). The elution fractions were then concentrated and then further purified by ion exchange using start buffer (20 mM TrisHCl, pH 8.5) and end buffer (20 mM TrisHCl, pH 8.5, 1 M NaCl). The fractions with optimum purity were recombined, concentrated by spin concentrated, supplemented with 10% glycerol and then stored at −80° C. for further application.

Results and Data Analysis

One-step affinity purification yielded proteins with only modest purity. After the second-step ion exchange, the purity was largely enhanced. The overall yield was estimated to be 0.1 mg per liter culture and the purity of the final products was 90% (FIG. 2 panels A-B). Surprisingly, the fusion proteins with the ZFP had higher protein expression and purification yields than fusion with the cell penetration peptides (TAT and Pep-1, FIG. 2, panel A).

This example shows that BoNTA-CPP fusion proteins can be expressed as a recombinant protein from *E. coli* and purified by affinity purification followed by ion exchange.

Example 2. Cleavage of Botulinum Substrates by BoNTA-CPP Fusion Proteins

This experiment demonstrates that the expressed BoNTA-CPP fusion proteins were active against BoNT substrate SNAP-25.

Botulinum Activity Test Using SNAPtide™ Assay

SNAPtide (Millipore, Cat. No. 567333-200NMOL) was diluted into 5 µM with reaction buffer (20 mM, pH 7.4, 0.25 mM ZnCl$_2$, 5 mM DTT, 0.05% Tween-20). Each of the recombinant BoNTA-ZFP fusion proteins (200 nM; Protein ID: 1~8) was added into reaction buffer containing SNAPtide. The reaction was incubated at 37° C. for 40 min. The fluorescence was recorded using a plate reader with an excitation wavelength of 320 nm and an emission wavelength of 420 nm. The SNAPtide was a short peptide derived from SNAP-25, the intracellular substrate of BoNTA. SNAPtide contained the cleavage site of BoNTA and both a fluorophore and a quencher groups. Cleavage of the peptide frees the fluorophore and activates fluorescence. Reaction positive control was a commercially available recombinant BoNTA light chain (BoNTA-LC) protein purchased from R&D Systems (Cat. No. 4489-ZN-010). All data were performed in three replicates.

Results and Data Analysis

The data in FIG. 3 are shown as mean±standard deviation and analyzed by one-tailed Student's t test. All tested samples, including the commercial BoNTA-LC, have significantly ($p<0.05$) higher signals than SNAPtide control group. As shown in FIG. 3, both single-end and bipartite fusion of ZFP retained the activity of BoNTA on the peptide substrate derived from SNAP-25.

Example 3. Cell Penetrating Activity Assay of BoNTA-ZFP Fusion Proteins

This experiment demonstrates that selected BoNTA-ZFP fusion proteins can effectively penetrate human dermal fibroblasts (hDF).

Transduction of hDF Cells with Recombinant BoNTA-ZFP Fusion Proteins hDF cells were seeded on to 6-well plates pre-coated with poly-lysine. At 24 h after seeding, cells were washed with phosphate buffered saline (PBS) for three times. BoNTA-ZFP proteins (Protein ID 5 and 6) and control protein (R&D BoNTA-LC, a commercially available light chain of BoNTA from R&D Systems) were diluted with DMEM serum-free medium. Cells were treated with BoNTA-ZFP proteins (0.15 µM) and BoNTA-LC (0.5 µM) at 37° C. for 2 h. The cells were then washed three times with PBS supplemented with 0.5 mg/mL heparin to remove surface-bound proteins and then harvested by trypsin treatment. The collected cells were lysed by sonication and the BoNTA activity was assayed as described above.

Results and Data Analysis

The data as presented in FIG. 4 are shown as mean±standard deviation and analyzed by one-tailed Student's t test. hDF cells treated with BoNTA-ZFP proteins (Protein ID 5 and 6) exhibited evident BoNTA activity, with significantly higher signals than the control group ($p<0.05$). This demonstrates that BoNTA-ZFP proteins could penetrate cells effectively.

Example 4. In Vivo Activity of BoNTA-ZFP Proteins in Mice

This experiment demonstrates that, when applied to intact or microneedle-treated mouse skin, BoNTA-ZFP fusion proteins can cause muscle paralysis, characterized by abduction of digits.

Digit Abduction Experiments

Fifteen C57 female mice with a weight of approximately 36 g were randomly divided into 5 groups (n=3). In all mice, the left legs were left untreated as a control and the right legs were treated with different drugs. Mice were anaesthetized before treatment. In mock group (A), mice were administrated with storage buffer (20 mM HEPES, pH 7.0, 300 mM NaCl and 10% glycerol). In BOTOX (Allergan) injection group (B), BOTOX was reconstituted with 0.9% NaCl saline as instructed and 5 µL of 45 U/mL solution was injected into the right legs. In group C, mice legs and feet were pre-treated with microneedle roller (RoHS MR20, 0.2 mm, house use) and then 60 µL of 45 U/mL BOTOX was topically applied. In group D, mice legs and feet were pre-treated with microneedle roller (RoHS MR20, 0.2 mm, house use) and then 60 μL of 0.05 mg/mL BoNTA-ZFP protein (Protein ID 6) in storage buffer (20 mM HEPES, pH 7.0, 300 mM NaCl and 10% glycerol) was topically applied. In group E, 60 μL of 0.05 mg/mL BoNTA-ZFP protein in storage buffer (20 mM HEPES, pH 7.0, 300 mM NaCl and 10% glycerol) was topically applied. Microneedle roller treatment was applied by rolling three times on legs and feet. When topically applied, legs and feet were uniformly spread with substances, massaged and then air dried, which was repeated for several times until all solution was administrated. Digit abduction was recorded after mice were awake at Day 0 and then recorded each day for the following four days.

Results and Data Analysis

Figure 5:
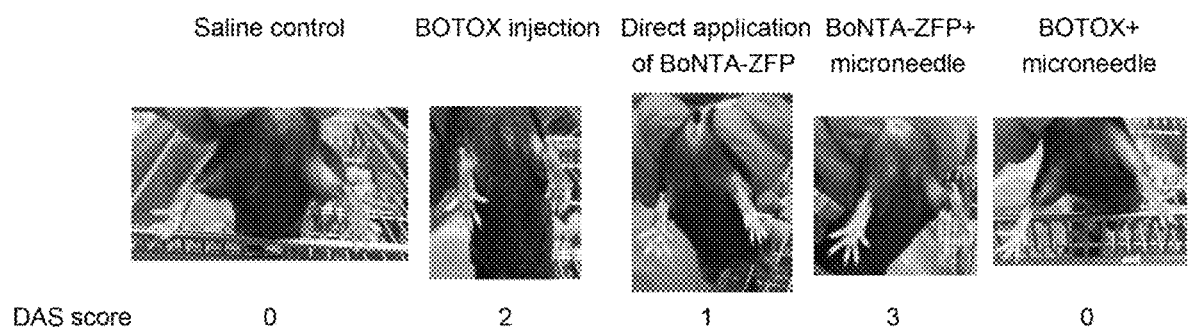
FIG. 5 presents representative images of the in vivo effects of cell-penetrating BoNTA proteins.
Figure 6:
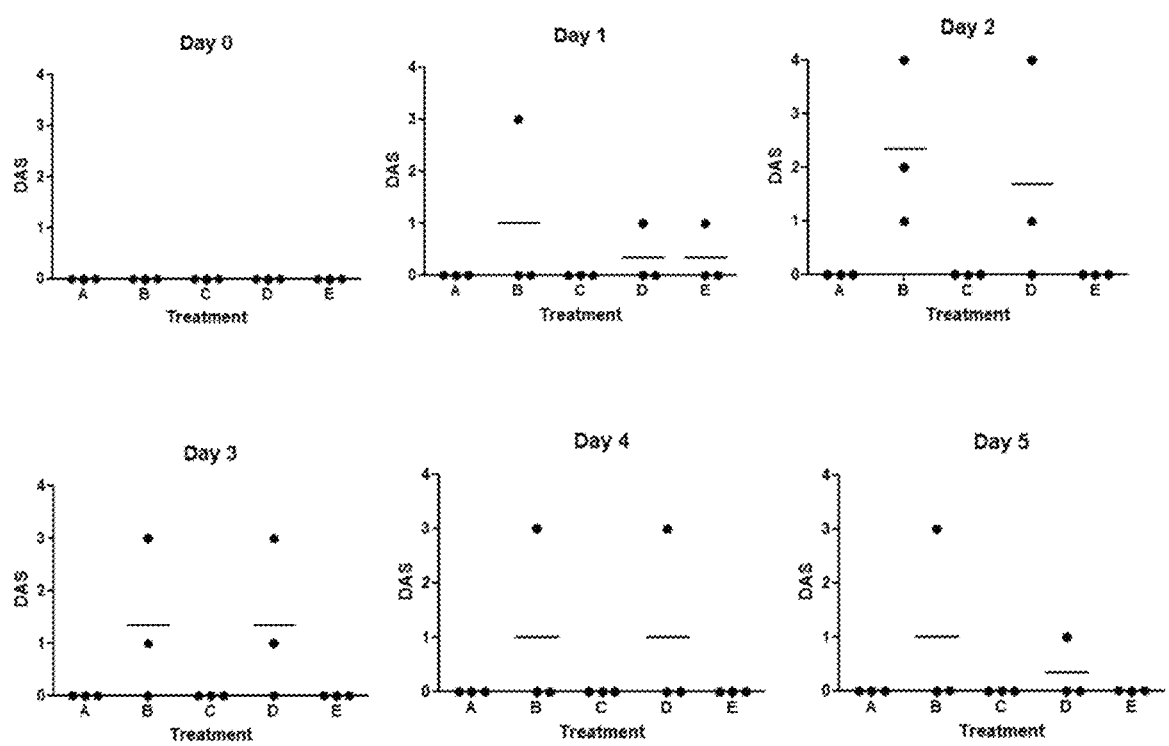
FIG. 6 presents scatter plots of digit abduction of mice treated with cell-penetrating BoNTA proteins. A, treated with 0.9% NaCl saline solution. B, injected with BOTOX. C, pre-treated with microneedle and then treated with BOTOX. D, pre-treated with microneedle and then treated with cell-penetrating BoNTA-ZFP (Protein ID 6). E, treated with cell-penetrating BoNTA-ZFP (Protein ID 6) without microneedle pre-treatment.

Both injectable BOTOX and BoNTA-ZFP with microneedle pre-treatment exhibited notable digit abduction (FIG. 5), with significantly higher scores than control group A ($p<0.05$; Student's t test). Direct application of BoNTA-ZFP resulted in minimal effect. The digit abduction score (DAS) was evaluated by three independent researchers in a blinded manner. The DAS reached peak value at Day 2 (FIG. 6). This example therefore shows that when applied on to mouse skin, cell-penetrating BoNTA-ZFP can cause muscle paralysis, indicative of in vivo activity of SNAP-25 cleavage.

Example 5. Expression in Insect Cells

This experiment demonstrates that BoNTA-ZFP fusion proteins can be expressed in insect cells with high yield. Considering that the native BoNTs are produced from bacterium *Clostridium botulinum* (prokaryotes), the high-quantity production of BoNTA from insect cells (eukaryotes) is truly surprising.

Methods pFastBac vectors containing Protein ID 6 (SEQ ID NO:15) was packaged into baculovirus (BV). BV containing recombinant Protein ID 6 protein was used to infect *Spodoptera frugiperda* Sf9 insect cells. Harvest cells when cell viability became below 60%. Approximately 1 mL of culture was centrifuged to collect cells. These cells were resuspended in 1 mL PBS buffer and sonicated. Approximately 10 μL of cell lysate was resolved on SDS-PAGE. The protein was detected using anti-His antibody and imaged.

Results and Data Analysis

Figure 7:
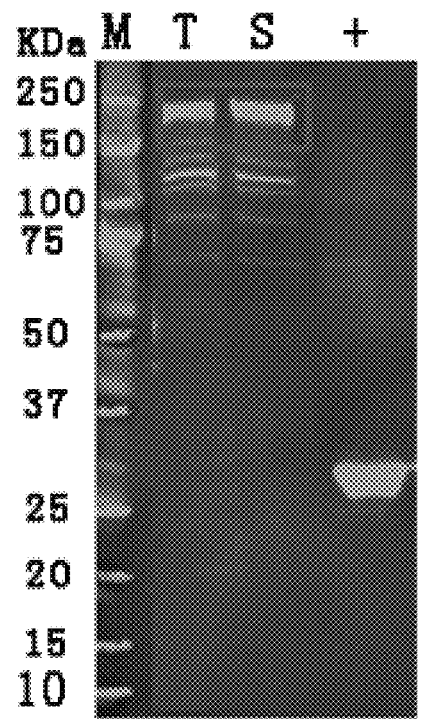
FIG. 7 shows expression of BoNTA-ZFP (Protein ID 6) in insect cells. M, protein marker. T, total cell lysate. S, soluble fraction. +, loading control.

The soluble BoNTA-ZF is near 100% of the total protein (FIG. 7). The amount of protein was quantified to be 1 μg as compared to the loading control (5 μg protein) (FIG. 7). Accordingly, the expression yield is calculated to be 100 mg per liter culture.

Example 6. Intramuscular Injection Causes Muscle Paralysis

Methods

BoNTA-ZFP of varying dosage was intramuscularly injected into the right gastrocnemius muscle using a Hamilton syringe. The muscle paralysis was monitored as described in Example 4.

Results and Data Analysis

Intramuscular injection of 1 or 3 ng of BoNTA-ZFP (Protein ID 6) led to apparent digit abduction. A score of 4 was reached for all mice (n=3 per group).

Example 7. Treadmill Tests

This example tests a method for measuring the muscle-paralyzing activities of agents. Compared with the voluntary running study, this method can objectively reflect the muscle-paralyzing activity of cell-penetrating BoNTA-ZFP.

Methods

BoNTA-ZFP was topically applied on to CJ57 female mice as described in Example 4. Mice were subjected into the following sequence of settings for angle and speed: 0°/5 m/min, 3°/8 m/min, 6°/11 m/min, 9°/14 m/min, 12°/17 m/min, 12°/20 m/min. Mice were maintained at each step for 5 min. The total distance was counted.

Results and Data Analysis

Figure 8:
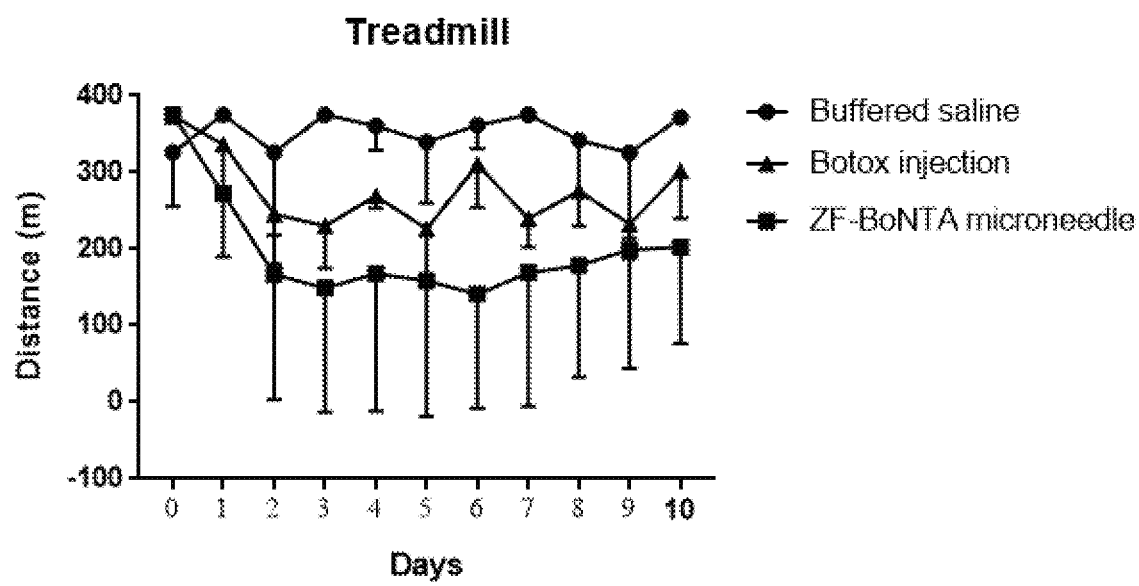
FIG. 8 presents testing results from a treadmill study for analyzing the muscle paralyzing activity of BoNTA-ZFP.

Mice treated with Botox injection or topical BoNTA-ZFP exhibited reduced motion ability on treadmill study as compared to buffered saline (FIG. 8).

Example 8. Beam Balance Tests

This example tests another method for measuring the muscle-paralyzing activities of agents.

Methods

BoNTA-ZFP was topically applied on to CJ57 female mice as described in Example 4. Mice were subjected into beam balance study. The time for mice to pass the beam was counted.

Results and Data Analysis

Figure 9:
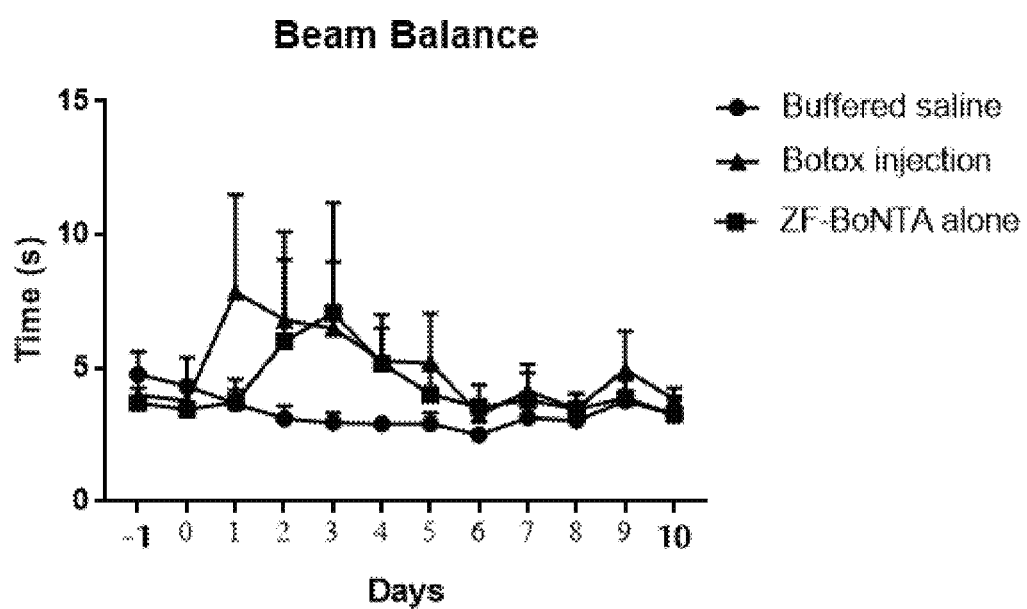
FIG. 9 presents testing results from a beam balance study for analyzing the muscle paralyzing activity of BoNTA-ZFP.

Mice treated with Botox injection or topical BoNTA-ZFP exhibited reduced motion ability on beam balance study as compared to buffered saline (FIG. 9).

Example 9. Footprint Tests

This example tests yet another method for measuring the muscle-paralyzing activities of agents.

Methods

BoNTA-ZFP was topically applied on to CJ57 female mice as described in Example 4. Mice were subjected into footprint analysis study. The width for footprint was recorded.

Results and Data Analysis

Figure 10:
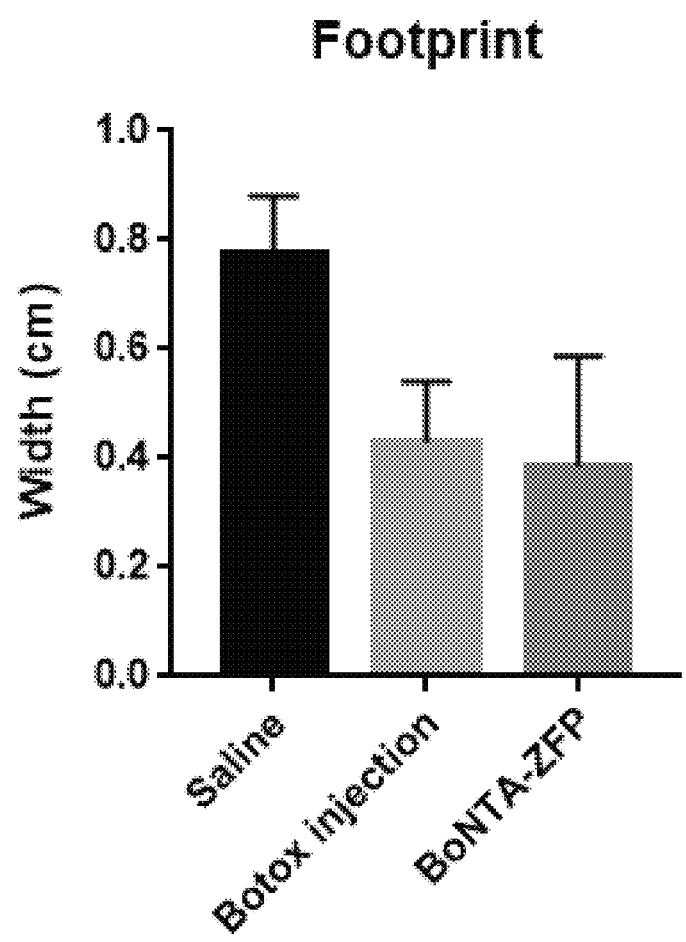
FIG. 10 presents testing results from a footprint study for analyzing the muscle paralyzing activity of BoNTA-ZFP.

Mice treated with Botox injection or topical BoNTA-ZFP exhibited reduced contact area on footprint analysis as compared to buffered saline (FIG. 10).

Examples 8-10 demonstrate the effectiveness and the quantitative nature of these tests for measuring the muscle-paralyzing activities of test agents.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. A chimeric polypeptide comprising (a) a botulinum toxin (BoNT) light chain, (b) a BoNT heavy chain, and (c) a zinc finger motif,
wherein
(i) the BoNT light chain, the BoNT heavy chain, and the zinc finger motif are within a same peptide chain which comprises, from the N-terminus to the C-terminus, the BoNT light chain, the BoNT heavy chain, and the zinc finger motif; or
(ii) the BoNT light chain and the BoNT heavy chain are on two separate peptide chains and are bound to each other through a disulfide bond, and one of the peptide chains further comprises the zinc finger motif that is C-terminal to the BoNT light chain or the BoNT heavy chain within the respective peptide chain.

2. The chimeric polypeptide of claim 1, wherein the zinc finger motif is on the same peptide chain as the BoNT heavy chain and is C-terminal to the BoNT heavy chain.

3. The chimeric polypeptide of claim 2, further comprising a second zinc finger motif on the same peptide chain as the BoNT light chain and is N-terminal to the BoNT light chain.

4. The chimeric polypeptide of claim 3, wherein each zinc finger motif is a Cys$_2$-His$_2$ zinc finger motif.

5. The chimeric polypeptide of claim 4, wherein each zinc finger motif comprises an alpha-helical fragment, and contains at least an alanine at one or more residues of −1, 2, 3 or 6 of the alpha-helical fragment.

6. The chimeric polypeptide of claim 3, wherein each zinc finger motif comprises an amino acid sequence selected from the group consisting of SEQ ID NO: 1 and 5 to 7.

7. The chimeric polypeptide of claim 6, wherein each zinc finger motif comprises the amino acid sequence of SEQ ID NO: 1.

8. The chimeric polypeptide of claim 3, wherein each zinc finger motif comprises the amino acid sequence of SEQ ID NO: 3.

9. The chimeric polypeptide of claim 8, wherein the BoNT light chain and the BoNT heavy chain are within the same protein chain.

10. The chimeric polypeptide of claim 8, wherein the BoNT light chain and the BoNT heavy chain are on separate protein chains connected through the disulfide bond.

11. The chimeric polypeptide of claim 1, wherein the BoNT is selected from BoNT A, B, C, D, E, F, or G.

12. The chimeric polypeptide of claim 11, wherein the BoNT is selected from subtypes of BoNT A1-A10, B1-B8, E1-E9, and F1-F7.

13. The chimeric polypeptide of claim 11, wherein the BoNT is BoNT A.

14. The chimeric polypeptide of claim 1, wherein the BoNT light chain comprises the amino acid sequence of SEQ ID NO: 8 or an amino sequence having at least 90% sequence identity to SEQ ID NO: 8.

15. The chimeric polypeptide of claim 1, wherein the BoNT heavy chain comprises the amino acid sequence of SEQ ID NO: 9 or an amino sequence having at least 90% sequence identity to SEQ ID NO: 9.

16. A method of administering a BoNT light chain to a mammal, comprising topically or intramuscularly applying a formulation comprising the chimeric polypeptide of claim 1.

17. The method of claim 16, wherein the topical application is on a skin or a mucous membrane of an eye, ear, nose, mouth, lip, urethral opening, anus, or tongue.

18. A formulation comprising a chimeric polypeptide of claim 1 and a pharmaceutically suitable carrier.

* * * * *